United States Patent
Bonda et al.

(10) Patent No.: US 7,799,317 B2
(45) Date of Patent: *Sep. 21, 2010

(54) PHOTOSTABILIZERS, UV ABSORBERS, AND METHODS OF PHOTOSTABILIZING COMPOSITIONS

(75) Inventors: Craig A. Bonda, Winfield, IL (US); Anna Pavlovic, Elmwood Park, IL (US)

(73) Assignee: Hallstar Innovations Corp., Chicago, IL (US)

( * ) Notice: Subject to any disclaimer, the term of this patent is extended or adjusted under 35 U.S.C. 154(b) by 1069 days.

This patent is subject to a terminal disclaimer.

(21) Appl. No.: 11/491,205

(22) Filed: Jul. 21, 2006

(65) Prior Publication Data

US 2006/0257338 A1 Nov. 16, 2006

Related U.S. Application Data

(63) Continuation-in-part of application No. 11/123,925, filed on May 6, 2005, now Pat. No. 7,544,350, which is a continuation-in-part of application No. 10/385,833, filed on Mar. 11, 2003, now Pat. No. 6,962,692, which is a continuation-in-part of application No. 10/302,423, filed on Nov. 22, 2002, now Pat. No. 6,800,274.

(51) Int. Cl.
 *A61K 8/18* (2006.01)
(52) U.S. Cl. .......................... 424/59; 558/410
(58) Field of Classification Search ............... 424/59; 558/410

See application file for complete search history.

(56) References Cited

U.S. PATENT DOCUMENTS

| | | | |
|---|---|---|---|
| 3,215,724 A | 11/1965 | Strobel et al. | 260/465 |
| 3,215,725 A | 11/1965 | Strobel et al. | 260/465 |
| 3,272,855 A | 9/1966 | Strobel et al. | 260/465 |
| 3,275,520 A | 9/1966 | Strobel et al. | 167/90 |
| 3,337,357 A | 8/1967 | Strobel et al. | 106/178 |
| 3,445,545 A | 5/1969 | Skoultchi | 260/881 |
| 3,860,700 A | 1/1975 | Viout et al. | 424/61 |
| 3,957,512 A * | 5/1976 | Kleeberg et al. | 430/325 |
| 3,992,356 A | 11/1976 | Jacquet et al. | 260/47 |
| 4,107,290 A | 8/1978 | Jacquet et al. | 424/47 |
| 4,128,536 A | 12/1978 | Brodsky et al. | 427/54 |
| 4,178,303 A | 12/1979 | Lorenz et al. | 260/465 |
| 4,202,834 A | 5/1980 | Gruber et al. | 260/465 |
| 4,202,836 A | 5/1980 | Gruber et al. | 260/465.4 |

(Continued)

FOREIGN PATENT DOCUMENTS

EP 0 675 875 11/1998

(Continued)

*Primary Examiner*—Kamal A Saeed
*Assistant Examiner*—Valerie Rodriguez-Garcia
(74) *Attorney, Agent, or Firm*—Marshall, Gerstein & Borun LLP

(57) ABSTRACT

Polymers containing one or more novel photoactive moieties, sunscreen compositions including a mixture of a photoactive compound and a polymer containing one or more photoactive moieties are described herein. Also disclosed are methods for stabilizing a sunscreen composition, methods of filtering out ultra-violet light from a substrate by the addition of one or more of the foregoing polymers, methods accepting the triplet excited state energy with one or more of the foregoing polymer, and methods of increasing the UV-A Protective Value are described herein.

40 Claims, 4 Drawing Sheets

U.S. PATENT DOCUMENTS

| | | | |
|---|---|---|---|
| 4,203,919 A | 5/1980 | Gruber et al. | 260/465 |
| 4,207,253 A | 6/1980 | Lorenz et al. | 260/465 |
| 4,218,392 A | 8/1980 | Lorenz et al. | 260/465 |
| 4,263,366 A | 4/1981 | Lorenz et al. | 428/332 |
| 4,276,136 A | 6/1981 | Gruber et al. | 204/159 |
| 4,868,246 A | 9/1989 | MacLeay et al. | 525/142 |
| 5,321,112 A | 6/1994 | Olson | 528/75 |
| 5,576,354 A | 11/1996 | Deflandre et al. | 514/685 |
| 5,821,380 A | 10/1998 | Holderbaum et al. | 558/443 |
| 5,989,528 A | 11/1999 | Tanner et al. | 424/59 |
| 6,033,649 A | 3/2000 | Gonzenbach et al. | 424/60 |
| 6,069,258 A | 5/2000 | Habeck et al. | 549/76 |
| 6,416,773 B2 | 7/2002 | Heidenfelder et al. | 424/401 |

FOREIGN PATENT DOCUMENTS

| | | |
|---|---|---|
| JP | 2004-243596 | 2/2004 |
| WO | WO 94/14760 | 7/1994 |
| WO | WO 01/16224 | 3/2001 |
| WO | WO 01/90233 | 11/2001 |
| WO | WO 02/42368 | 5/2002 |

\* cited by examiner

US 7,799,317 B2

PHOTOSTABILIZERS, UV ABSORBERS, AND METHODS OF PHOTOSTABILIZING COMPOSITIONS

CROSS-REFERENCE TO RELATED APPLICATIONS

This is a continuation-in-part of U.S. patent application Ser. No. 11/123,925, filed May 6, 2005, which is a continuation-in-part of U.S. patent application Ser. No. 10/385,833, filed Mar. 11, 2003, and issued Nov. 8, 2005 as U.S. Pat. No. 6,962,692, which is a continuation-in-part of U.S. patent application Ser. No. 10/302,423, filed Nov. 22, 2002 and issued Mar. 25, 2004 as U.S. Pat. No. 6,800,274, the disclosures of which are hereby incorporated herein by reference.

BACKGROUND

1. Field of the Technology

The invention relates to compounds which absorb ultraviolet (UV) light, sunscreen compositions of these compounds, methods of protecting human skin from UV radiation, methods of photostabilzing a dibenzoylmethane derivative, and methods of quenching triplet excited state energy. More particularly, the invention relates to novel polymers terminated with α-cyano acrylates, acrylamides, and/or thioacrylates.

2. Brief Description of Related Technology

It is well known that UV radiation having a wavelength from about 280 nm or 290 nm to about 320 nm (UV-B) is harmful to human skin, causing burns that are detrimental to the development of a good suntan. UV-A radiation (about 320 nm to about 400 nm), while producing tanning of the skin, also can cause damage, particularly to very lightly colored or sensitive skin, leading to reduction of skin elasticity and wrinkles. Therefore, a sunscreen composition for use on human skin preferably includes both a UV-A and a UV-B filter to prevent most of the sunlight within the full range of about 280 nm to about 400 nm from damaging human skin.

Ultraviolet radiation from the sun or artificial sources can also cause harm to coatings containing photoactive substances, such as photoactive pigments and dyes, by breaking down chemical bonds in the structure of a component such as a polymer, a pigment, or a dye. This photodegradation can lead to yellowing, color fading, loss of gloss, and loss of physical and protective properties of a coating. Photodegradation can take place in several steps which include one or more components of a coating absorbing UV radiation. The absorbed radiation can excite the absorbing molecules and raise them to a higher energy level, which can be very reactive. If the molecule cannot be relaxed, bond cleavage and the formation of free radicals will occur. These free radicals can attack one or more color molecules and/or a polymer backbone and form more free radicals. UV-A and UV-B filters can also be used to absorb UV radiation to protect a pigmented coating.

The UV-B filters that are most widely used in the U.S. in commercial sunscreen compositions are paramethoxycinnamic acid esters, such as 2-ethylhexyl paramethoxycinnamate, commonly referred to as octyl methoxycinnamate or PARSOL MCX, octyl salicylate, and oxybenzone.

The organic UV-A filters most commonly used in commercial sunscreen compositions are the dibenzoylmethane derivatives, particularly 4-(1,1dimethylethyl)-4' methoxydibenzoylmethane (also called avobenzone, sold under the brand name PARSOL 1789). Other dibenzoylmethane derivatives described as UV-A filters are disclosed in U.S. Pat. Nos. 4,489,057, 4,387,089 and 4,562,067, the disclosures of which are hereby incorporated herein by reference. It is also well known that the above described UV-A filters, particularly the dibenzoylmethane derivatives, can suffer from rapid photochemical degradation, when used alone or when combined with the above described most commercially used UV-B filters.

Typically, the above described UV-B filters are combined with the above described UV-A filters in a solution with other lipophilic or oily ingredients. This solution of oily ingredients, known to formulators of cosmetic products including sunscreens as the "oil phase," is typically, but not necessarily, dispersed with the help of emulsifiers and stabilizers into an aqueous solution composed primarily of water, to make an emulsion which becomes a final cream or lotion form of a sunscreen composition.

The performance of a photoactive compound or a combination of photoactive compounds in a sunscreen composition has been extremely difficult to predict based on the levels of photoactive compounds in the formulation, particularly when the formulation includes one or more photoactive compounds that suffer from relatively rapid photodegradation, such as avobenzone. Because of this, each formulation has required expensive laboratory testing to determine the UV absorbance, as a function of time (quantity) of exposure of the formulation to UV radiation. Moreover, a particularly difficult problem is presented when one photoactive compound in a sunscreen composition acts to increase the rate of photodegradation of another photoactive compound in the composition. This can be accomplished in a number or ways, including a bimolecular reaction between two photoactive compounds and a lowering of the threshold energy need to raise a photoactive compound to its excited state. For example, when avobenzone is combined with octyl methoxycinnamate a bimolecular pathway leads to the rapid photodegradation of both the dibenzoylmethane derivative and the octyl methoxycinnamate.

Methods and compositions for stabilizing photoactive compounds, such as dibenzoylmethane derivatives with the use of diesters and/or polyesters of naphthalene dicarboxylic acid are described in U.S. Pat. Nos. 5,993,789, and 6,284,916, the disclosures of which are hereby incorporated herein by reference. Other methods of stabilizing a dibenzoylmethane derivative include the addition of a α-cyano-β, β-diphenylacrylate compound to a sunscreen composition that includes a dibenzoylmethane derivative. See, Deflandre et al, U.S. Pat. No. 5,576,354 and Gonzenbach et al., U.S. Pat. No. 6,033,649.

SUMMARY

One aspect of the compounds, compositions, and methods described herein is a polymeric compound terminated with α-cyano acrylates, acrylamides, and/or thioacrylates, such as a compound of formula (I) as described below.

Another aspect of the compounds, compositions, and methods described herein is a sunscreen composition including a photoactive compound and a polymeric compound terminated with α-cyano acrylates, acrylamides, and/or thioacrylates, such as a compound of formula (I) as described below.

Another aspect of the compounds, compositions, and methods described herein is a method of protecting a surface from ultra-violet light including applying a polymeric compound terminated with α-cyano acrylates, acrylamides, and/ or thioacrylates, such as a compound of formula (I) as described below, or a composition containing the same to the surface.

Yet another aspect of the compounds, compositions, and methods described herein is a method of photostabilizing a dibenzoylmethane derivative by adding a polymeric compound terminated with α-cyano acrylates, acrylamides, and/ or thioacrylates, such as a compound of formula (I) as described below, to a composition containing a dibenzoylmethane derivative.

Yet another aspect of the compounds, compositions, and methods described herein is a method of quenching triplet excited state energy from a triplet-excited photoactive compound in a sunscreen composition by adding to the composition a polymeric compound terminated with α-cyano acrylates, acrylamides, and/or thioacrylates, such as a compound of formula (I) as described below.

Still another aspect of the compounds, compositions, and methods described herein is methods of increasing or "boosting" the UV-A protective value of the compositions by adding to the composition a polymer terminated with a α-cyano acrylates, acrylamides, and/or thioacrylates, such as a compound of formula (I) as described below.

DETAILED DESCRIPTION OF THE PREFERRED EMBODIMENTS

Figure 1:
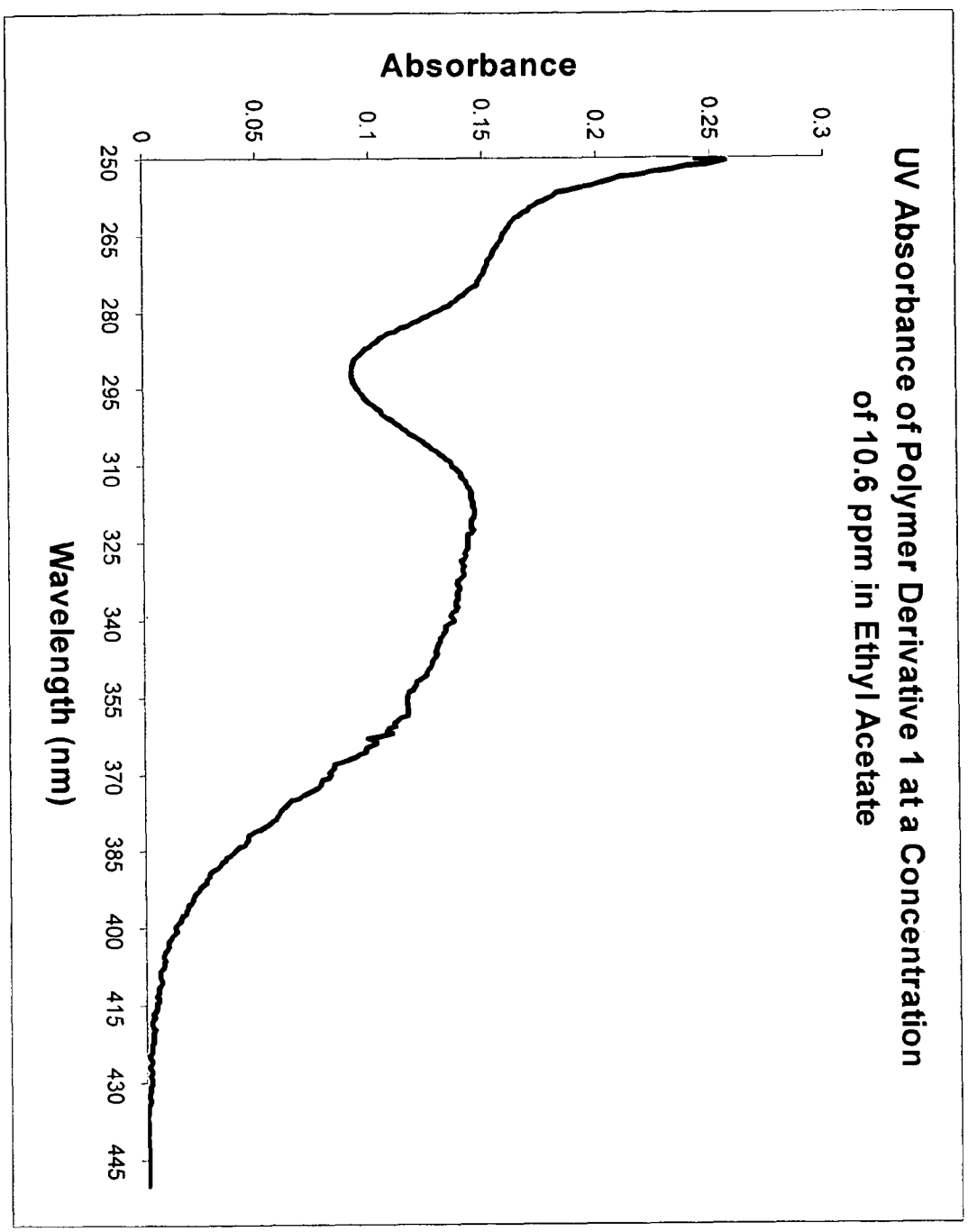
FIG. 1 is a graph of the absorbance of Polymer Derivative 1 (an α-cyano β-p-methoxyphenyl β-napthyl acrylate terminated polymer) at a concentration of 10.6 ppm and from a wavelength of 250 nm to 450 nm.

Photostabilzing polymers having at least one α-cyano β-aryl acrylate or acrylate derivative, sunscreen compositions having a photostabilzing polymer and one or more photoactive compound, such as a dibenzoylmethane derivative UV-A filter compound, are described herein. One aspect of the sunscreen compositions described herein are methods of photostabilizing a sunscreen composition including a dibenzoylmethane derivative, such as 4-(1,1-dimethylethyl)-4'-methoxydibenzoylmethane (PARSOL® 1789/Avobenzone), wherein one or more photoactive compounds present in a sunscreen composition (e.g., Avobenzone) are made more photostable by the addition of a polymer having at least one α-cyano β-aryl acrylate or acrylate derivative. Also disclosed herein are methods for filtering out ultra-violet light from human skin including the step of applying a polymer having at least one α-cyano β-aryl acrylate or acrylate derivative to the skin. Also disclosed herein are methods for increasing or "boosting" the UV-A protective value of a sunscreen composition including the step of applying a polymer having at least one α-cyano β-aryl acrylate or acrylate derivative to the skin.

A photoactive compound can be considered stable when, for example, after 30 MED irradiation the photoactive compound has retained at least about 90% of its original absorbance at a wavelength or a range of wavelengths of interest (e.g., the wavelength at which or near a photoactive compound has a peak absorbance, such as 350-370 nm for avobenzone). Likewise, a sunscreen composition can include a plurality of photoactive compounds and a sunscreen composition, as a whole, can be considered stable when, for example, after 30 MED irradiation the sunscreen composition has retained at least about 90% of its original absorbance at one or more wavelengths of interest (e.g., at or near the peak absorbance wavelength of the primary photoactive compounds).

It has surprisingly been found that the addition of one or more of a polymer having at least one α-cyano β, β-diaryl acrylate or acrylate derivative increases the photostability of the sunscreen composition and/or photounstable components present therein. Without intending to be limited to any particular mechanism of achieving this increase in stability, it is believed that such compounds, such as the compounds of formula (I) described below, stabilize a photounstable component of a sunscreen composition (e.g., a dibenzoylmethane derivative) by accepting the triplet excited state energy of a dibenzoylmethane derivative that has reached an excited state as a result of the absorption of ultra-violet light. Once a dibenzoylmethane derivative is excited, it is prone to degrade according to a number of pathways; however, the degradation of the dibenzoylmethane derivative can be substantially reduced or prevented when a polymer terminated with an α-cyano β, β-diaryl acrylate derivative, such as the compounds of formula (I) described below, is added to quench (accept) the triplet excited state energy present in an excited dibenzoylmethane molecule. Thus, in one pathway of degradation, a dibenzoylmethane derivative is excited to its triplet state and the excited state triplet energy is released in a bond breaking step, thereby preventing the dibenzoylmethane derivative from further accepting ultra-violet radiation. A polymer terminated with an α-cyano β, β-diaryl acrylate derivative, such as the compounds of formula (I) described below, stabilizes a dibenzoylmethane derivative by accepting the triplet (excited state) energy of the excited dibenzoylmethane derivative in such a way as to convert the excited dibenzoylmethane derivative back to a ground state that is capable of reaccepting ultra-violet radiation (energy transfer). Without intending to be limited to any particular mechanism by which a such compounds are able to quench (accept the excited state energy) an excited photoactive compound, it is believed that a polymer terminated with an α-cyano β, β-diaryl acrylate derivative, such as the compounds of formula (I) described below, accepts the excited state energy and dissipates the energy kinetically in the form of rapid isomerizations. An example of this process is shown below:

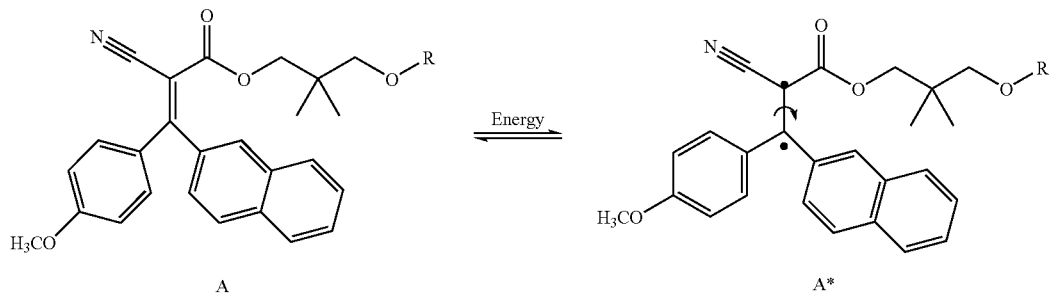

wherein the compound designated A above is an acrylate polymer (R represents the rest of the polyester compound formed from the combination of neopentyl glycol and adipic acid (see Examples 1 and 2 below), accepts the triplet excited state energy and forms a diradical (shown above as A*) at the α and β positions of the acrylate, which converts the double bond into a single bond and allows for free rotation about the single bond. This rotation occurs rapidly and efficiently to dissipate excited state energy accepted by the polymer terminated with an α-cyano β, β-diaryl acrylate derivative, such as the compounds of formula (I) described below.

A sunscreen composition disclosed herein can be combined into a cosmetically acceptable carrier, optionally including emollients, stabilizers, emulsifiers, such as those known in the art, and combinations thereof. These additives can be used in preparing an emulsion from an aqueous system and a mixture of a filter system that includes one or more photoactive compounds and a solvent system that includes one or more organic solvents. When made, preferably the emulsion is an oil-in-water emulsion, wherein the oil phase is primarily formed from a mixture of the filter system and solvent system.

A typical sunscreen composition includes one or more photoactive compounds, wherein a photoactive compound acts to absorb UV radiation and thereby protect the substrate (e.g., human skin) from the harmful effects of UV radiation. The absorption process causes a photoactive compound to reach an excited state, wherein the excited state is characterized by the presence of excited energy (e.g., singlet energy or triplet energy), as compared to the ground state of the photoactive compound. Once a photoactive compound reaches an excited state there exists a number of pathways by which the excited photoactive compound can dissipate its excess energy (e.g., triplet energy), however, many of those pathways adversely affect the ability of the photoactive compound to further absorb UV radiation.

A photoactive compound is one that responds to light photoelectrically. In the compositions disclosed herein, a photoactive compound is one that responds to UV radiation photoelectrically. For example, photoactive compounds that respond to UV radiation photoelectrically by rapid photodegradation can benefit highly from the compositions and methods disclosed herein, even though the benefits of the compositions and methods disclosed herein are not limited to such compounds. Photostability is a potential problem with all UV filters because they are deliberately selected as UV absorbing molecules. In other applications, a photoactive compound may be a pigment or a dye (e.g., a hydrophobic dye).

UV filters include compounds selected from the following categories (with specific examples) including: p-aminobenzoic acid, its salts and its derivatives (ethyl, isobutyl, glyceryl esters; p-dimethylaminobenzoic acid); anthranilates (o-aminobenzoates; methyl, menthyl, phenyl, benzyl, phenylethyl, linalyl, terpinyl, and cyclohexenyl esters); salicylates (octyl, amyl, phenyl, benzyl, menthyl (homosalate), glyceryl, and dipropyleneglycol esters); cinnamic acid derivatives (menthyl and benzyl esters, alpha-phenyl cinnamonitrile; butyl cinnamoyl pyruvate); dihydroxycinnamic acid derivatives (umbelliferone, methylumbelliferone, methylaceto-umbelliferone); camphor derivatives (3-benzylidene, 4-methylbenzylidene, polyacrylamidomethyl benzylidene, benzalkonium methosulfate, benzylidene camphor sulfonic acid, and terephthalylidene dicamphor sulfonic acid); trihydroxycinnamic acid derivatives (esculetin, methylesculetin, daphnetin, and the glucosides, esculin and daphnin); hydrocarbons (diphenylbutadiene, stilbene); dibenzalacetone; benzalacetophenone; naphtholsulfonates (sodium salts of 2-naphthol-3,6-disulfonic and of 2-naphthol-6,8-disulfonic acids); dihydroxy-naphthoic acid and its salts; o- and p-hydroxydiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric acid derivatives; vilouric acid derivatives; tannic acid and its derivatives; hydroquinone; and benzophenones (oxybenzone, sulisobenzone, dioxybenzone, benzoresorcinol, 2,2',4,4'-tetrahydroxybenzophenone, 2,2'-dihydroxy-4,4'-dimethoxybenzophenone, octabenzone, 4-isopropyldibenzoylmethane, butylmethoxydibenzoylmethane, etocrylene, and 4-isopropyl-dibenzoylmethane).

Particularly useful are: 2-ethylhexyl p-methoxycinnamate, 4,4'-t-butyl methoxydibenzoylmethane, 2-hydroxy-4-methoxybenzophenone, octyldimethyl p-aminobenzoic acid, digalloyltrioleate, 2,2-dihydroxy-4-methoxybenzophenone, ethyl 4-[bis(hydroxypropyl)]aminobenzoate, 2-ethylhexyl-2-cyano-3,3-diphenylacrylate, 2-ethylhexylsalicylate, glycerol p-aminobenzoate, 3,3,5-trimethylcyclohexylsalicylate, methylanthranilate, p-dimethylaminobenzoic acid or aminobenzoate, 2-ethylhexyl p-dimethylaminobenzoate, 2-phenylbenzimidazole-5-sulfonic acid, 2-(p-dimethylaminophenyl-sulfoniobenzoxazoic acid, and combinations thereof.

For a product marketed in the United States, preferred cosmetically-acceptable photoactive compounds and concentrations (reported as a percentage by weight of the total cosmetic sunscreen composition) include: aminobenzoic acid (also called para-aminobenzoic acid and PABA; 15% or less), avobenzone (also called butyl methoxy dibenzoylmethane; 3% or less), cinoxate (also called 2-ethoxyethyl p-methoxycinnamate; 3% or less), dioxybenzone (also called benzophenone-8; 3% or less), homosalate (15% or less), menthyl anthranilate (also called menthyl 2-aminobenzoate; 5% or less), octocrylene (also called 2-ethylhexyl-2-cyano-3,3diphenylacrylate; 10% or less), octyl methoxycinnamate (7.5% or less), octyl salicylate (also called 2-ethylhexyl salicylate; 5% or less), oxybenzone (also called benzophenone-3; 6% or less), padimate O (also called octyl dimethyl PABA; 8% or less), phenylbenzimidazole sulfonic acid (water soluble; 4% or less), sulisobenzone (also called benzophenone-4; 10% or less), titanium dioxide (25% or less), trolamine salicylate (also called triethanolamine salicylate; 12% or less), and zinc oxide (25% or less).

Other preferred cosmetically-acceptable photoactive compounds and preferred concentrations (percent by weight of the total cosmetic sunscreen composition) include diethanolamine methoxycinnamate (10% or less), ethyl-[bis(hydroxypropyl)] aminobenzoate (5% or less), glyceryl aminobenzoate (3% or less), 4-isopropyl dibenzoylmethane (5% or less), 4-methylbenzylidene camphor (6% or less), terephthalylidene dicamphor sulfonic acid (10% or less), and sulisobenzone (also called benzophenone-4, 10% or less).

For a product marketed in the European Union, preferred cosmetically-acceptable photoactive compounds and preferred concentrations (reported as a percentage by weight of the total cosmetic sunscreen composition) include: PABA (5% or less), camphor benzalkonium methosulfate (6% or less), homosalate (10% or less), benzophenone-3 (10% or less), phenylbenzimidazole sulfonic acid (8% or less, expressed as acid), terephthalidene dicamphor sulfonic acid (10% or less, expressed as acid), butyl methoxydibenzoylmethane (5% or less), benzylidene camphor sulfonic acid (6% or less, expressed as acid), octocrylene (10% or less, expressed as acid), polyacrylamidomethyl benzylidene camphor (6% or less), ethylhexyl methoxycinnamate (10% or less), PEG-25 PABA (10% or less), isoamyl p-methoxycinnamate (10% or less), ethylhexyl triazone (5% or less), drometrizole trielloxane (15% or less), diethylhexyl butamido triazone (10% or less), 4-methylbenzylidene camphor (4% or less), 3-benzylidene camphor (2% or less), ethylhexyl salicylate (5% or less), ethylhexyl dimethyl PABA (8% or less), benzophenone-4 (5%, expressed as acid), methylene bis-benztriazolyl tetramethylbutylphenol (10% or less), disodium phenyl dibenzimidazole tetrasulfonate (10% or less, expressed as acid), bis-ethylhexyloxyphenol methoxyphenol triazine (10% or less), methylene bisbenzotriazolyl tetramethylbutylphenol (10% or less, also called TINOSORB M), and bisethylhexyloxyphenol methoxyphenyl triazine (10% or less, also called TINOSORB S).

All of the above-described UV filters are commercially available. For example, suitable commercially-available organic UV filters are identified by trade name and supplier in Table I below:

TABLE I

| CTFA Name | Trade Name | Supplier |
| --- | --- | --- |
| benzophenone-3 | UVINUL M-40 | BASF Chemical Co. |
| benzophenone-4 | UVINUL ® MS-40 | BASF Chemical Co. |
| benzophenone-8 | SPECTRA-SORB ® UV-24 | American Cyanamid |
| DEA-methoxycinnamate | BERNEL HYDRO | Bernel Chemical |
| ethyl dihydroxypropyl-PABA | AMERSCREEN ® P | Amerchol Corp. |
| glyceryl PABA | NIPA G.M.P.A. | Nipa Labs. |
| homosalate | KEMESTER ® HMS | Humko Chemical |
| menthyl anthranilate | SUNAROME ® UV-A | Felton Worldwide |
| octocrylene | UVINUL ® N-539 | BASF Chemical Co. |
| octyl dimethyl PABA | AMERSCOL | Amerchol Corp. |
| octyl methoxycinnamate | PARSOL MCX | Bernel Chemical |
| PABA | PABA | National Starch |
| 2-phenylbenzimidazole-5-sulphonic acid | EUSOLEX ® 6300 | EM Industries |
| TEA salicylate | SUNAROME ® W | Felton Worldwide |
| 2-(4-methylbenzildene)-camphor | EUSOLEX ® 6300 | EM Industries |
| diethylamino hydroxybenzoyl hexyl benzoate | UVINUL ® A Plus | BASF Chemical Co. |
| benzophenone-1 | UVINUL ® 400 | BASF Chemical Co. |
| benzophenone-2 | UVINUL ® D-50 | BASF Chemical Co. |
| benzophenone-6 | UVINUL ® D-49 | BASF Chemical Co. |
| benzophenone-12 | UVINUL ® 408 | BASF Chemical Co. |
| 4-isopropyl dibenzoyl methane | EUSOLEX 8020 | EM Industries |
| disodium phenyl dibenzimidazole tetrasulfonate | NEO HELIOPAN ® AP | Symrise GmbH & Co. |
| butyl methoxy dibenzoyl methane | PARSOL ® 1789 | Givaudan Corp. |
| etocrylene | UVINUL ® N-35 | BASF Chemical Co. |
| methylene bisbenzotriazolyl tetramethylbutylphenol | TINOSORB ® M | Ciba Specialty Chemicals |
| bisethylhexyloxyphenol methoxyphenyl triazine. | TINOSORB ® S | Ciba Specialty Chemicals |

The term "alkyl" as used herein refers to straight- and branched-chain hydrocarbon groups, preferably containing one to thirty carbon atoms. Examples of alkyl groups are $C_1$-$C_4$ alkyl groups. As used herein the designation $C_x$-$C_y$, wherein x and y are integers, denotes a group having from x to y carbon atoms, e.g., a $C_1$-$C_4$ alkyl group is an alkyl group having one to four carbon atoms. Nonlimiting examples of alkyl groups include, methyl, ethyl, n-propyl, isopropyl, n-butyl, sec-butyl (2-methylpropyl), t-butyl (1,1-dimethylethyl), and 3,3-dimethylpentane.

The term "cycloalkyl" as used herein refers to an aliphatic cyclic hydrocarbon group, preferably containing three to eight carbon atoms. Nonlimiting examples of cycloalkyl groups include cyclopropyl, cyclobutyl, cyclopentyl, and cyclohexyl.

The term "alkenyl" as used herein includes both straight chained, branched, and cyclic hydrocarbon radicals that include at least one carbon-carbon double bond, preferably, an alkenyl group contains between two and thirty carbon atoms. Nonlimiting examples alkenyl groups include methylene, ethylene, propylene, butylene, and isopropylene.

The terms "alkyne" and "alkynyl" as used herein include both straight and branched chained hydrocarbon radicals having at least one carbon-carbon triple bond, preferably, an alkyne group contains between two and thirty carbon atoms.

The term "polyether" as used herein refers to a group with at least two ethers present in a carbon chain. Nonlimiting examples of polyethers include 1-butoxy-2-methoxyethane, 1-butoxy-2-(2-methoxyethoxy)ethane, 2-(2-methoxyethoxy)-1-(2-methylpentyloxy)propane, and 1-(2-methylpentyloxy)-2-(2-pentyloxyethoxy)propane.

The terms "substituted alkyl," "substituted cycloalkyl," "substituted alkenyl," "substituted alkynyl," and "substituted polyether" as used herein refer to an alkyl, cycloalkyl, alkenyl, alkyne, or polyether group having one or more substituents. Substituents can include, but are not limited to, alkyl, cycloalkyl, alkenyl, alkyne, polyether, substituted polyether, heteroaryl, heterocycloalkyl, aryl, substituted aryl, substituted heteroaryl, substituted heterocycloalkyl, hydroxyl, ester, carboxy, cyano, amino, amido, sulfur, and halo. Preferred substituted alkyl groups have one to twenty carbon atoms, not including carbon atoms of the substituent group. Preferably, a substituted alkyl group is mono- or di-substituted at one, two, or three carbon atoms. The substituents can be bound to the same carbon or different carbon atoms.

The terms "ester" and "alkoxycarbonyl" as used herein refer to a group of the general formula:

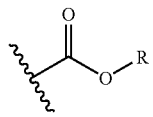

wherein R is an alkyl group, alkenyl group, alkyne group, cycloalkyl group, polyether, aryl, substituted alkyl group, substituted alkenyl group, substituted alkyne group, substituted cycloalkyl group, substituted aryl group, substituted heteroaryl, substituted heterocycloalkyl, or substituted polyether group.

The term "aryl" as used herein refers to monocyclic, fused bicyclic, and fused tricyclic carbocyclic aromatic ring systems including, but not limited to, phenyl, naphthyl, tetrahydronaphthyl, phenanthrenyl, biphenylenyl, indanyl, indenyl, anthracenyl, and fluorenyl.

The term "heteroaryl" as used herein refers to monocyclic, fused bicyclic, and fused tricyclic aromatic ring systems, wherein one to four-ring atoms are selected from the group consisting of oxygen, nitrogen, and sulfur, and the remaining ring atoms are carbon, the ring system being joined to the remainder of the molecule by any of the ring atoms. Nonlimiting examples of heteroaryl groups include, but are not limited to, pyridyl, pyrazinyl, pyrimidinyl, pyrrolyl, pyrazolyl, imidazolyl, thiazolyl, tetrazolyl, oxazolyl, isooxazolyl, thiadiazolyl, oxadiazolyl, thiophenyl, furanyl, quinolinyl, isoquinolinyl, benzoxazolyl, benzimidazolyl, and benzothiazolyl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The terms "substituted aryl," "substituted heteroaryl," and "substituted heterocycloalkyl" as used herein refer to an aryl, heteroaryl, or heterocycloalkyl group substituted by a replacement of one, two, three, or four of the hydrogen atoms thereon with a substitute selected from the group consisting of alkyl, alkenyl, alkyne, substituted alkyl, substituted cycloalkyl, substituted alkenyl, substituted alkyne, ether, amino, aryl, heteroaryl, cycloalkyl, heterocycloalkyl, $O(CH_2)_{1-3}N(R)_2$, $O(CH_2)_{1-3}CO_2H$, hydroxyl, ester, carboxy, cyano, amino, amido, sulfur, and halo.

The term "amino" as used herein refers to an —$NH_2$ or —NH— group, wherein each hydrogen in each formula can be replaced with an alkyl, cycloalkyl, aryl, polyether, heteroaryl, heterocycloalkyl, substituted alkyl, substituted cycloalkyl, substituted aryl, substituted polyether, substituted heteroaryl, or substituted heterocycloalkyl group, i.e., $N(R)_2$. In the case of —$NH_2$, the hydrogen atoms also can be replaced with substituents taken together to form a 5- or 6-membered aromatic or non-aromatic ring, wherein one or two carbons of the ring optionally are replaced with a heteroatom selected from the group consisting of sulfur, oxygen, and nitrogen. The ring also optionally can be substituted with an alkyl group. Examples of rings formed by substituents taken together with the nitrogen atom include morpholinyl, phenylpiperazinyl, imidazolyl, pyrrolidinyl, (N-methyl)piperazinyl, and piperidinyl.

The term "amido" as used herein refers to a moiety of the general formula:

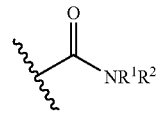

wherein $R^1$ and $R^2$ are the same or different and selected from hydrogen, alkyl, alkenyl, alkyne, substituted alkyl, substituted alkenyl, substituted alkyne, aryl, alkenyl aryl, heteroaryl, and alkenyl heteroaryl.

The term "cyano" as used herein refers to a —C≡N group, also designated —CN.

The term "halo" as used herein refers to fluorine, chlorine, bromine, and iodine.

The term "carboxy" or "carboxylate" as used herein refers to a moiety of the general formula:

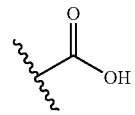

wherein the hydrogen of the above moiety may optionally be substituted with a metal ion to form a carboxylate salt. Such metal ions include, but are not limited to, sodium, calcium, lithium, potassium, magnesium, and the like.

The term "hydroxyl" as used herein refers to an —OH group.

The term "alkoxy" as used herein refers to an —Oalkyl group, wherein alkyl represents a group as defined above.

The term "alkylcarbonyl as used herein refers to a moiety of the general formula:

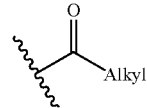

wherein alkyl is defined above.

The term "oxycarbonyl" as used herein refers to a moiety of formula —OC(O)R, where R is an alkyl, cycloalkyl, alkenyl, alkynyl, aryl, polyether, heteroaryl, heterocycloalkyl, substituted alkyl, substituted cycloalkyl, substituted aryl, substituted polyether, substituted heteroaryl, or substituted heterocycloalkyl group.

The term "thioether" as used herein refers to a moiety of formul —SR, wherein R is an alkyl, cycloalkyl, alkenyl, alkynyl, aryl, polyether, heteroaryl, heterocycloalkyl, substituted alkyl, substituted cycloalkyl, substituted aryl, substituted polyether, substituted heteroaryl, or substituted heterocycloalkyl group.

The term "Polycrylene®" as used herein refers to a polymeric compound with the following Chemical Abstract Index name: Hexanedioic acid, polymer with 2,2-dimethyl-1,3-propanediol, 3-[(2-cyano-1-oxo-3,3-diphenyl-2-propenyl)oxy]-2,2-dimethylpropyl 2-octyldodecyl ester (CAS Reg. No. 862993-96-2). Polycrylene® and methods for making the same are described in the commonly assigned U.S. Pat. Nos. 6,962,692 and 6,800,274, and is available from The C.P. Hall Company and affiliates thereof (Chicago, Ill.).

A sunscreen composition described herein can include a variety of photoactive compounds, including one or more UV-A photoactive compounds and one or more UV-B photoactive compounds. Preferably, a sunscreen composition includes a photoactive compound selected from the group consisting of p-aminobenzoic acid and salts and derivatives thereof; anthranilate and derivatives thereof; dibenzoylmethane and derivatives thereof; salicylate and derivatives thereof; cinnamic acid and derivatives thereof; dihydroxycinnamic acid and derivatives thereof; camphor and salts and derivatives thereof; trihydroxycinnamic acid and derivatives thereof; dibenzalacetone naphtholsulfonate and salts and derivatives thereof; benzalacetophenone naphtholsulfonate and salts and derivatives thereof; dihydroxy-naphthoic acid and salts thereof; o-hydroxydiphenyldisulfonate and salts and derivatives thereof; p-hydroxydiphenyldisulfonate and salts and derivatives thereof; coumarin and derivatives thereof; diazole derivatives; quinine derivatives and salts thereof; quinoline derivatives; hydroxy-substituted benzophenone derivatives; methoxy-substituted benzophenone derivatives; uric acid derivatives; vilouric acid derivatives; tannic acid and derivatives thereof; hydroquinone; benzophenone derivatives; 1,3,5-triazine derivatives, phenyldibenzimidazole tetrasulfonate and salts and derivatives thereof; terephthalylidene dicamphor sulfonic acid and salts and derivatives thereof; methylene bis-benzotriazolyl tetramethylbutylphenol and salts and derivatives thereof; bis-ethylhexyloxyphenol methoxyphenyl triazine and salts and derivatives thereof; diethylamino hydroxybenzoyl hexyl benzoate and salts and derivatives thereof; and combinations of the foregoing.

It has been found that in a sunscreen composition described herein a compound of formula (I) is preferably combined with a photoactive agent selected from the group consisting of bis-ethylethoxyphenol-methoxyphenol triazine, methylene bis-benzotriazolyl tetramethylbutyl phenol, diethylamino-hydroxybenzoyl-hexyl benzoate, disodium phenyldibenzimidazoletetrasulfonate, octocrylene, di-octyl-naphthalate, and combinations thereof. More preferably, the composition includes a photoactive compound that absorbs in the UV-A range (about 320 nm to about 400 nm), such as those described below.

UV-A radiation (about 320 nm to about 400 nm) is recognized as contributing to causing damage, particularly to very lightly-colored or sensitive skin. A sunscreen composition described herein preferably includes a UV-A photoactive compound. Preferably, a sunscreen composition disclosed herein includes a dibenzoylmethane derivative UV-A photoactive compound. Preferred dibenzoylmethane derivatives include, 2-methyldibenzoylmethane; 4-methyldibenzoylmethane; 4-isopropyldibenzoylmethane; 4-tert-butyldibenzoylmethane; 2,4-dimethyldibenzoylmethane; 2,5-dimethyldibenzoylmethane; 4,4'-diisopropyldibenzoylmethane; 4,4'-dimethoxydibenzoylmethane; 4-tert-butyl-4'-methoxydibenzoylmethane; 2-methyl-5-isopropyl-4'-methoxydibenzoylmethane; 2-methyl-5-tert-butyl-4'-methoxydibenzoylmethane; 2,4-dimethyl-4'-methoxydibenzoylmethane; 2,6-dimethyl-4-tert-butyl-4'-methoxydibenzoylmethane, and combinations thereof.

It has been found, quite surprisingly, that substitutions on the aromatic rings at the beta positions on the acrylate moieties with an electron donating substituent causes an increase in the polymers' ability to stabilize a photounstable compound in a composition. Without intending to be limited to any particular mechanism of achieving this increase in stability, it is believed that electron donating substituents on the aryl rings increases the stability of the proposed diradical that forms upon excitation, and thereby allows for a more efficient kinetic dissipation of the excited state energy. Thus, the beta positions on the acrylate moieties present in the polymers described herein are preferably selected from the group consisting of naphthyl, phenyl, substituted naphthyl, substituted phenyl, heteroaryl, substituted heteroaryl, and combinations thereof. More preferably, selected from the group consisting of substituted naphthyl, substituted phenyl, and substituted heteroaryl, and combinations thereof. Still more preferably each aromatic ring contains at least one electron donating substituents. Suitable electron donating substituents include, but are not limited to alkyl, alkenyl, aryl, alkoxy, amino, alkylamino, thioether, hydroxyl, oxycarbonyl, and amido.

One embodiment of the compounds, compositions and methods described herein is a compound of formula (I):

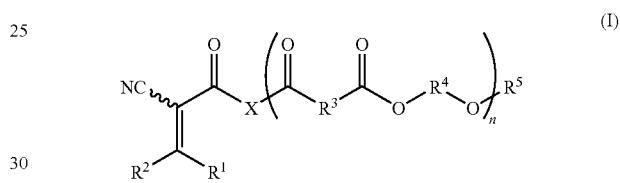

(I)

wherein $R^2$ is (a) phenyl substituted with 0, 1, 2, 3, or 4 $R^6$ substituents or (b) 1-naphthyl or 2-naphthyl substituted with 0, 1, 2, 3, or 4 $R^6$ substituents; $R^1$ is selected from the group consisting of hydrogen, $C_1$-$C_{50}$ alkyl, $C_2$-$C_{50}$ alkenyl, $C_2$-$C_{50}$ alkynyl, $C_3$-$C_8$ cycloalkyl, $C_2$-$C_7$ heterocycloalkyl, aryl, $C_1$-$C_{50}$ polyether, $C_1$-$C_{50}$ substituted alkyl, $C_3$-$C_8$ substituted cycloalkyl, $C_2$-$C_{50}$ substituted alkenyl, $C_2$-$C_{50}$ substituted alkynyl, $C_2$-$C_7$ substituted heterocycloalkyl, substituted aryl, heteroaryl, and substituted heteroaryl; $R^3$ and $R^4$ are the same or different and are selected from the group consisting of $C_1$-$C_{30}$ alkyl, $C_3$-$C_8$ cycloalkyl, substituted alkyl, substituted cycloalkyl, aryl, heteroaryl, heterocycloalkyl, substituted aryl, substituted heteroaryl, and substituted heterocycloalkyl; X is selected from the group consisting of O—$C_1$-$C_{20}$ alkyl-O—, N($R^7$)—$C_1$-$C_{20}$ alky-N($R^7$)—, and S—$C_1$-$C_{20}$ alkyl-S—; $R^7$ is selected from the group consisting of hydrogen and $C_1$-$C_{20}$ alkyl; $R^5$ is selected from the group consisting of $C_3$-$C_{50}$ alkyl, $C_2$-$C_{50}$ alkenyl, $C_2$-$C_{50}$ alkynyl, $C_3$-$C_8$ cycloalkyl, $C_2$-$C_7$ heterocycloalkyl, aryl, $C_1$-$C_{50}$ polyether, $C_1$-$C_{50}$ substituted alkyl, $C_3$-$C_8$ substituted cycloalkyl, $C_2$-$C_{50}$ substituted alkenyl, $C_2$-$C_{50}$ substituted alkynyl, $C_2$-$C_7$ substituted heterocycloalkyl, substituted aryl, heteroaryl, substituted heteroaryl, and a structure of formula (II):

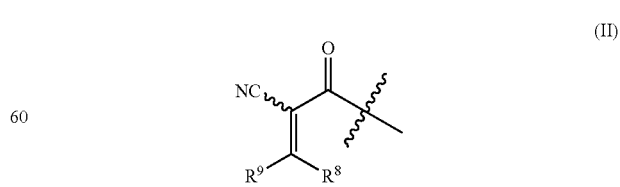

(II)

$R^9$ is (a) phenyl substituted with 0, 1, 2, 3, or 4 $R^{10}$ substituents or (b) 1-naphthyl or 2-naphthyl substituted with 0, 1, 2, 3, or 4 $R^{10}$ substituents; $R^6$ and $R^{10}$ are the same or different and are selected from the group consisting of hydrogen, hydroxyl, alkyl, alkenyl, alkynyl, alkoxy, halo, ester, nitro, nitroso, alkylcarbonyl, alkoxycarbonyl, aryl, amino, substituted amino, amido, substituted amido, sulfate, carboxylate, oxycarbonyl, cycloalkyl, haloalkyl, cyano, and thioether; $R^8$ is selected from the group consisting of hydrogen, $C_2$-$C_{50}$ alkyl, $C_2$-$C_{50}$ alkenyl, $C_2$-$C_{50}$ alkynyl, $C_3$-$C_8$ cycloalkyl, $C_2$-$C_7$ heterocycloalkyl, aryl, $C_1$-$C_{50}$ polyether, $C_1$-$C_{50}$ substituted alkyl, $C_3$-$C_8$ substituted cycloalkyl, $C_2$-$C_{50}$ substituted alkenyl, $C_2$-$C_{50}$ substituted alkynyl, $C_2$-$C_7$ substituted heterocycloalkyl, substituted aryl, heteroaryl, and substituted heteroaryl; and n is an integer from 1 to 500.

Another embodiment of a sunscreen composition disclosed herein includes a mixture of a photoactive compound and a compound of formula (I):

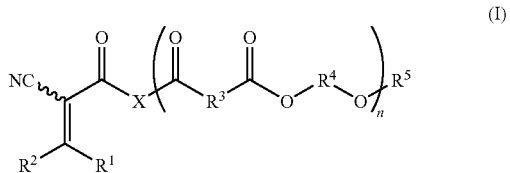

(I)

wherein $R^2$ is (a) phenyl substituted with 0, 1, 2, 3, or 4 $R^6$ substituents or (b) 1-naphthyl or 2-naphthyl substituted with 0, 1, 2, 3, or 4 $R^6$ substituents; $R^1$ is hydrogen, $C_1$-$C_{50}$ alkyl, $C_2$-$C_{50}$ alkenyl, $C_2$-$C_{50}$ alkynyl, $C_3$-$C_8$ cycloalkyl, $C_2$-$C_7$ heterocycloalkyl, aryl, $C_1$-$C_{50}$ polyether, $C_1$-$C_{50}$ substituted alkyl, $C_3$-$C_8$ substituted cycloalkyl, $C_2$-$C_{50}$ substituted alkenyl, $C_2$-$C_{50}$ substituted alkynyl, $C_2$-$C_7$ substituted heterocycloalkyl, substituted aryl, heteroaryl, or substituted heteroaryl; $R^3$ and $R^4$ are the same or different and are $C_1$-$C_{30}$ alkyl, $C_3$-$C_8$ cycloalkyl, substituted alkyl, substituted cycloalkyl, aryl, heteroaryl, heterocycloalkyl, substituted aryl, substituted heteroaryl, or substituted heterocycloalkyl; X is O—$C_1$-$C_{20}$ alkyl-O—, N($R^7$)—$C_1$-$C_{20}$ alky-N($R^7$)—, and S—$C_1$-$C_{20}$ alkyl-S—; $R^7$ is hydrogen or $C_1$-$C_{20}$ alkyl; $R^5$ is $C_3$-$C_{50}$ alkyl, $C_2$-$C_{50}$ alkenyl, $C_2$-$C_{50}$ alkynyl, $C_3$-$C_8$ cycloalkyl, $C_2$-$C_7$ heterocycloalkyl, aryl, $C_1$-$C_{50}$ polyether, $C_1$-$C_{50}$ substituted alkyl, $C_3$-$C_8$ substituted cycloalkyl, $C_2$-$C_{50}$ substituted alkenyl, $C_2$-$C_{50}$ substituted alkynyl, $C_2$-$C_7$ substituted heterocycloalkyl, substituted aryl, heteroaryl, substituted heteroaryl, or a structure of formula (II):

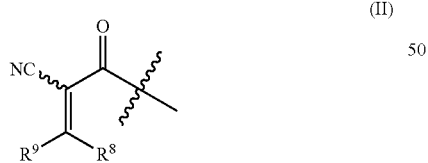

(II)

$R^9$ is (a) phenyl substituted with 0, 1, 2, 3, or 4 $R^{10}$ substituents or (b) 1-naphthyl or 2-naphthyl substituted with 0, 1, 2, 3, or 4 $R^{10}$ substituents; $R^6$ and $R^{10}$ are the same or different and are hydrogen, hydroxyl, alkyl, alkenyl, alkynyl, alkoxy, halo, ester, nitro, nitroso, alkylcarbonyl, alkoxycarbonyl, aryl, amino, substituted amino, amido, substituted amido, sulfate, carboxylate, oxycarbonyl, cycloalkyl, haloalkyl, cyano, or thioether; $R^8$ is hydrogen, $C_2$-$C_{50}$ alkyl, $C_2$-$C_{50}$ alkenyl, $C_2$-$C_{50}$ alkynyl, $C_3$-$C_8$ cycloalkyl, $C_2$-$C_7$ heterocycloalkyl, aryl, $C_1$-$C_{50}$ polyether, $C_1$-$C_{50}$ substituted alkyl, $C_3$-$C_8$ substituted cycloalkyl, $C_2$-$C_{50}$ substituted alkenyl, $C_2$-$C_{50}$ substituted alkynyl, $C_2$-$C_7$ substituted heterocycloalkyl, substituted aryl, heteroaryl, or substituted heteroaryl; and n is an integer from 1 to 500.

Another embodiment of the compounds, compositions, and methods described herein is a method of protecting a surface from ultraviolet radiation, including topically applying to the surface, in a cosmetically acceptable carrier, a compound of formula (I):

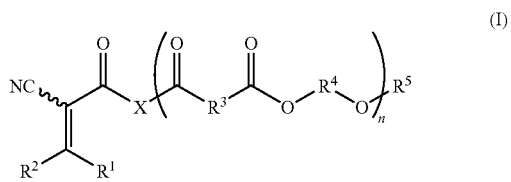

(I)

wherein $R^2$ is (a) phenyl substituted with 0, 1, 2, 3, or 4 $R^6$ substituents or (b) 1-naphthyl or 2-naphthyl substituted with 0, 1, 2, 3, or 4 $R^6$ substituents; $R^1$ is selected from the group consisting of hydrogen, $C_1$-$C_{50}$ alkyl, $C_2$-$C_{50}$ alkenyl, $C_2$-$C_{50}$ alkynyl, $C_3$-$C_8$ cycloalkyl, $C_2$-$C_7$ heterocycloalkyl, aryl, $C_1$-$C_{50}$ polyether, $C_1$-$C_{50}$ substituted alkyl, $C_3$-$C_8$ substituted cycloalkyl, $C_2$-$C_{50}$ substituted alkenyl, $C_2$-$C_{50}$ substituted alkynyl, $C_2$-$C_7$ substituted heterocycloalkyl, substituted aryl, heteroaryl, and substituted heteroaryl; $R^3$ and $R^4$ are the same or different and are selected from the group consisting of $C_1$-$C_{30}$ alkyl, $C_3$-$C_8$ cycloalkyl, substituted alkyl, substituted cycloalkyl, aryl, heteroaryl, heterocycloalkyl, substituted aryl, substituted heteroaryl, and substituted heterocycloalkyl; X is selected from the group consisting of O—$C_1$-$C_{20}$ alkyl-O—, N($R^7$)—$C_1$-$C_{20}$ alky-N($R^7$)—, and S—$C_1$-$C_{20}$ alkyl-S—; $R^7$ is selected from the group consisting of hydrogen and $C_1$-$C_{20}$ alkyl; $R^5$ is selected from the group consisting of $C_3$-$C_{50}$ alkyl, $C_2$-$C_{50}$ alkenyl, $C_2$-$C_{50}$ alkynyl, $C_3$-$C_8$ cycloalkyl, $C_2$-$C_7$ heterocycloalkyl, aryl, $C_{1-C50}$ polyether, $C_{1-C50}$ substituted alkyl, $C_3$-$C_8$ substituted cycloalkyl, $C_2$-$C_{50}$ substituted alkenyl, $C_2$-$C_{50}$ substituted alkynyl, $C_2$-$C_7$ substituted heterocycloalkyl, substituted aryl, heteroaryl, substituted heteroaryl, and a structure of formula (II):

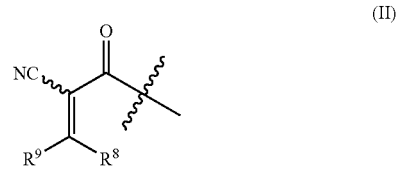

(II)

$R^9$ is (a) phenyl substituted with 0, 1, 2, 3, or 4 $R^{10}$ substituents or (b) 1-naphthyl or 2-naphthyl substituted with 0, 1, 2, 3, or 4 $R^{10}$ substituents; $R^6$ and $R^{10}$ are the same or different and are selected from the group consisting of hydrogen, hydroxyl, alkyl, alkenyl, alkynyl, alkoxy, halo, ester, nitro, nitroso, alkylcarbonyl, alkoxycarbonyl, aryl, amino, substituted amino, amido, substituted amido, sulfate, carboxylate, oxycarbonyl, cycloalkyl, haloalkyl, cyano, and thioether; $R^8$ is selected from the group consisting of hydrogen, $C_2$-$C_{50}$ alkyl, $C_2$-$C_{50}$ alkenyl, $C_2$-$C_{50}$ alkynyl, $C_3$-$C_8$ cycloalkyl, $C_2$-$C_7$ heterocycloalkyl, aryl, $C_1$-$C_{50}$ polyether, $C_1$-$C_{50}$ substituted alkyl, $C_3$-$C_8$ substituted cycloalkyl, $C_2$-$C_{50}$ substituted alkenyl, $C_2$-$C_{50}$ substituted alkynyl, $C_2$-$C_7$ substituted heterocycloalkyl, substituted aryl, heteroaryl, and substituted heteroaryl; and n is an integer from 1 to 500.

As used herein, the term "cosmetically acceptable carrier" refers to a carrier which is suitable for use in contact with tissues (e.g., the skin) without undue toxicity, incompatibility, instability, irritation, allergic response, and the like.

As described above, dibenzoylmethane derivatives tend to become unstable when exposed to UV radiation. It has been found, quite surprisingly, that the compound described herein are capable of stabilizing a dibenzoylmethane derivative present in a sunscreen composition. Accordingly, another embodiment of the compound, compositions, and methods described herein is a method of photostabilizing a dibenzoylmethane derivative, the method including the step of adding to the dibenzoylmethane derivative a photostabilizing amount of a compound of formula (I):

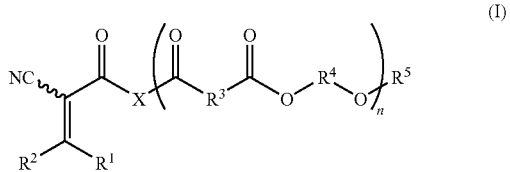

(I)

wherein $R^2$ is (a) phenyl substituted with 0, 1, 2, 3, or 4 $R^6$ substituents or (b) 1-naphthyl or 2-naphthyl substituted with 0, 1, 2, 3, or 4 $R^6$ substituents; $R^1$ is selected from the group consisting of hydrogen, $C_1$-$C_{50}$ alkyl, $C_2$-$C_{50}$ alkenyl, $C_2$-$C_{50}$ alkynyl, $C_3$-$C_8$ cycloalkyl, $C_2$-$C_7$ heterocycloalkyl, aryl, $C_1$-$C_{50}$ polyether, $C_1$-$C_{50}$ substituted alkyl, $C_3$-$C_8$ substituted cycloalkyl, $C_2$-$C_{50}$ substituted alkenyl, $C_2$-$C_{50}$ substituted alkynyl, $C_2$-$C_7$ substituted heterocycloalkyl, substituted aryl, heteroaryl, and substituted heteroaryl; $R^3$ and $R^4$ are the same or different and are selected from the group consisting of $C_1$-$C_{30}$ alkyl, $C_3$-$C_8$ cycloalkyl, substituted alkyl, substituted cycloalkyl, aryl, heteroaryl, heterocycloalkyl, substituted aryl, substituted heteroaryl, and substituted heterocycloalkyl; X is selected from the group consisting of O—$C_1$-$C_{20}$ alkyl-O—, $N(R^7)$—$C_1$-$C_{20}$ alky-$N(R^7)$—, and S—$C_1$-$C_{20}$ alkyl-S—; $R^7$ is selected from the group consisting of hydrogen and $C_1$-$C_{20}$ alkyl; $R^5$ is selected from the group consisting of $C_3$-$C_{50}$ alkyl, $C_2$-$C_{50}$ alkenyl, $C_2$-$C_{50}$ alkynyl, $C_3$-$C_8$ cycloalkyl, $C_2$-$C_7$ heterocycloalkyl, aryl, $C_1$-$C_{50}$ polyether, $C_1$-$C_{50}$ substituted alkyl, $C_3$-$C_8$ substituted cycloalkyl, $C_2$-$C_{50}$ substituted alkenyl, $C_2$-$C_{50}$ substituted alkynyl, $C_2$-$C_7$ substituted heterocycloalkyl, substituted aryl, heteroaryl, substituted heteroaryl, and a structure of formula (II):

(II)

$R^9$ is (a) phenyl substituted with 0, 1, 2, 3, or 4 $R^{10}$ substituents or (b) 1-naphthyl or 2-naphthyl substituted with 0, 1, 2, 3, or 4 $R^{10}$ substituents; $R^6$ and $R^{10}$ are the same or different and are selected from the group consisting of hydrogen, hydroxyl, alkyl, alkenyl, alkynyl, alkoxy, halo, ester, nitro, nitroso, alkylcarbonyl, alkoxycarbonyl, aryl, amino, substituted amino, amido, substituted amido, sulfate, carboxylate, oxycarbonyl, cycloalkyl, haloalkyl, cyano, and thioether; $R^8$ is selected from the group consisting of hydrogen, $C_2$-$C_{50}$ alkyl, $C_2$-$C_{50}$ alkenyl, $C_2$-$C_{50}$ alkynyl, $C_3$-$C_8$ cycloalkyl, $C_2$-$C_7$ heterocycloalkyl, aryl, $C_1$-$C_{50}$ polyether, $C_1$-$C_{50}$ substituted alkyl, $C_3$-$C_8$ substituted cycloalkyl, $C_2$-$C_{50}$ substituted alkenyl, $C_2$-$C_{50}$ substituted alkynyl, $C_2$-$C_7$ substituted heterocycloalkyl, substituted aryl, heteroaryl, and substituted heteroaryl; and n is an integer from 1 to 500.

It has been found that the polymeric compounds described herein are capable of accepting the triplet excited state energy of an excited photoactive compound. Accordingly, another embodiment of the compounds, compositions, and methods described herein is a method of quenching triplet excited state energy from a triplet-excited photoactive compound in a sunscreen composition comprising adding to the composition a compound of formula (I):

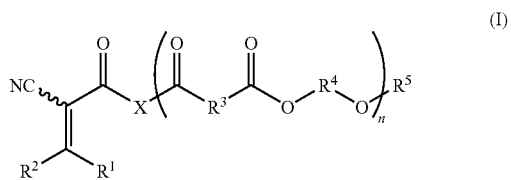

(I)

wherein $R^2$ is (a) phenyl substituted with 0, 1, 2, 3, or 4 $R^6$ substituents or (b) 1-naphthyl or 2-naphthyl substituted with 0, 1, 2, 3, or 4 $R^6$ substituents; $R^1$ is selected from the group consisting of hydrogen, $C_1$-$C_{50}$ alkyl, $C_2$-$C_{50}$ alkenyl, $C_2$-$C_{50}$ alkynyl, $C_3$-$C_8$ cycloalkyl, $C_2$-$C_7$ heterocycloalkyl, aryl, $C_1$-$C_{50}$ polyether, $C_1$-$C_{50}$ substituted alkyl, $C_3$-$C_8$ substituted cycloalkyl, $C_2$-$C_{50}$ substituted alkenyl, $C_2$-$C_{50}$ substituted alkynyl, $C_2$-$C_7$ substituted heterocycloalkyl, substituted aryl, heteroaryl, and substituted heteroaryl; $R^3$ and $R^4$ are the same or different and are selected from the group consisting of $C_1$-$C_{30}$ alkyl, $C_3$-$C_8$ cycloalkyl, substituted alkyl, substituted cycloalkyl, aryl, heteroaryl, heterocycloalkyl, substituted aryl, substituted heteroaryl, and substituted heterocycloalkyl; X is selected from the group consisting of O—$C_1$-$C_{20}$ alkyl-O—, $N(R^7)$—$C_1$-$C_{20}$ alky-$N(R^7)$—, and S—$C_1$-$C_{20}$ alkyl-S—; $R^7$ is selected from the group consisting of hydrogen and $C_1$-$C_{20}$ alkyl; $R^5$ is selected from the group consisting of $C_3$-$C_{50}$ alkyl, $C_2$-$C_{50}$ alkenyl, $C_2$-$C_{50}$ alkynyl, $C_3$-$C_8$ cycloalkyl, $C_2$-$C_7$ heterocycloalkyl, aryl, $C_1$-$C_{50}$ polyether, $C_1$-$C_{50}$ substituted alkyl, $C_3$-$C_8$ substituted cycloalkyl, $C_2$-$C_{50}$ substituted alkenyl, $C_2$-$C_{50}$ substituted alkynyl, $C_2$-$C_7$ substituted heterocycloalkyl, substituted aryl, heteroaryl, substituted heteroaryl, and a structure of formula (II):

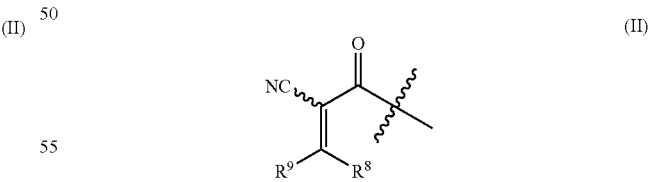

(II)

$R^9$ is (a) phenyl substituted with 0, 1, 2, 3, or 4 $R^{10}$ substituents or (b) 1-naphthyl or 2-naphthyl substituted with 0, 1, 2, 3, or 4 $R^{10}$ substituents; $R^6$ and $R^{10}$ are the same or different and are selected from the group consisting of hydrogen, hydroxyl, alkyl, alkenyl, alkynyl, alkoxy, halo, ester, nitro, nitroso, alkylcarbonyl, alkoxycarbonyl, aryl, amino, substituted amino, amido, substituted amido, sulfate, carboxylate, oxycarbonyl, cycloalkyl, haloalkyl, cyano, and thioether; $R^8$ is selected from the group consisting of hydrogen, $C_2$-$C_{50}$ alkyl, $C_2$-$C_{50}$ alkenyl, $C_2$-$C_{50}$ alkynyl, $C_3$-$C_8$ cycloalkyl, $C_2$-$C_7$ heterocycloalkyl, aryl, $C_1$-$C_{50}$ polyether, $C_1$-$C_{50}$ substituted alkyl, $C_3$-$C_8$ substituted cycloalkyl, $C_2$-$C_{50}$ substituted alkenyl, $C_2$-$C_{50}$ substituted alkynyl, $C_2$-$C_7$ substituted heterocycloalkyl, substituted aryl, heteroaryl, and substituted heteroaryl; and n is an integer from 1 to 500.

Several methods have been used to determine the "UV-A Protective Value" of a sunscreen composition. These include the in vitro methods known as "Critical Wavelength," "UV-A/UV-B ratio," "UV-A Index Method" as proposed by DKG (German Society for Scientific and Applied Cosmetics)—Task Force "Sun Protection", and the "Australian Standard" as determined by a "Solution" or "Thin Film Method." They also include the in vivo methods known as "Immediate Pigment Darkening" (IPD) and "Persistent Pigment Darkening" (PPD), the latter being the method recommended by the Japan Cosmetic Industry Association (JCIA) and used in Japan to measure for labeling purposes the UV-A protection efficacy of a sunscreen product. Though not officially recognized in the U.S. and Europe, the JCIA protocol is widely employed in both the U.S. and Europe to measure and compare the UV-A protective efficacy of sunscreen compositions. The UV-A Protective Value is often expressed as a value as determined by the particular method used. For example, UV-A Protective Values are often expressed as some value "PFA," "PA+++," "PPD," or "IPD." All of these and other expressions of the UV-A Protective Value are contemplated by the use of the term "UV-A Protective Value" throughout this disclosure. The following articles, which are all hereby incorporated herein by reference, describe these and other methods for determining the UV-A Protection Value: Ferrero et al., *Int. J. Cosmet. Sci.*, 24, 63-70 (2002); Kelley et al., *J. Soc. Cosmet. Chem.*, 44, 139-151 (1993); Ming-Thau et al., *J. Food & Drug Anal.*, 11, 128-132 (2003); Heiner Gers-Barlag, The Reproducibility of an In-Vitro Determination of the UVA INDEX Describing the Relative UVA Protection of Sun Care Products, *IFSCC Magazine*, vol. 5, no. 3 (2002); Pissavini et al., *Cosm. & Toil.*, 118, 63-71 (2003); "Boots of the Chemist Ltd., The Revised Guidelines to the Practical Measurement of UVA/UVB rations according to the Boots star rating system," The Boots, Co. PLC, Nottingham, England (2004); Diffey et al., *Int. J. Cosmet. Sci.*, 16, 47-52 (1994); Wendel et al., *SOFW-Journal*, 127, 12-30 (2001); Gers-Barlag et al., *International Sun Protection Conference, The Royal Society, London* (2005); Dippe et al., *SOFW-Journal*, 131, 36-44 (2005); Refregier, *International Sun Protection Conference, The Royal Society, London* (2003).

It has been found, quite surprisingly, that adding a polymer terminated with an α-cyano β, β-diaryl acrylate derivative, such as the compounds of formula (I) described below, increases the UV-A Protective Value. As shown in Table III below, a sunscreen composition containing 4% by weight of Polymer Derivative 1 and 3% by weight of Avobenzone achieved an average UV-A Protection Value of 12.35 using the Persistent Pigment Darkening method (PPD), which was 3.4 times greater than the PPD standard formulation's UV-A Protection Value on the same subjects. Accordingly, another embodiment of the compounds, compositions, and methods described herein is a method of increasing the UV-A Protection Value of a sunscreen composition containing at least one photoactive compound including the step of adding a compound of formula (I) to said composition:

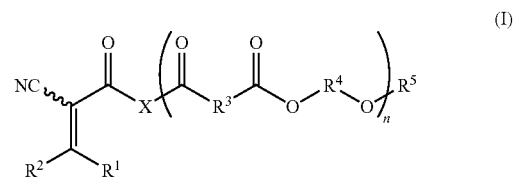

wherein $R^2$ is (a) phenyl substituted with 0, 1, 2, 3, or 4 $R^6$ substituents or (b) 1-naphthyl or 2-naphthyl substituted with 0, 1, 2, 3, or 4 $R^6$ substituents; $R^1$ is selected from the group consisting of hydrogen, $C_1$-$C_{50}$ alkyl, $C_2$-$C_{50}$ alkenyl, $C_2$-$C_{50}$ alkynyl, $C_3$-$C_8$ cycloalkyl, $C_2$-$C_7$ heterocycloalkyl, aryl, $C_1$-$C_{50}$ polyether, $C_1$-$C_{50}$ substituted alkyl, $C_3$-$C_8$ substituted cycloalkyl, $C_2$-$C_{50}$ substituted alkenyl, $C_2$-$C_{50}$ substituted alkynyl, $C_2$-$C_7$ substituted heterocycloalkyl, substituted aryl, heteroaryl, and substituted heteroaryl; $R^3$ and $R^4$ are the same or different and are selected from the group consisting of $C_1$-$C_{30}$ alkyl, $C_3$-$C_8$ cycloalkyl, substituted alkyl, substituted cycloalkyl, aryl, heteroaryl, heterocycloalkyl, substituted aryl, substituted heteroaryl, and substituted heterocycloalkyl; X is selected from the group consisting of O—$C_1$-$C_{20}$ alkyl-O—, N($R^7$)—$C_1$-$C_{20}$ alky-N($R^7$)—, and S—$C_1$-$C_{20}$ alkyl-S—; $R^7$ is selected from the group consisting of hydrogen and $C_1$-$C_{20}$ alkyl; $R^5$ is selected from the group consisting of $C_3$-$C_{50}$ alky, $C_2$-$C_{50}$ alkenyl, $C_2$-$C_{50}$ alkynyl, $C_3$-$C_8$ cycloalkyl, $C_2$-$C_7$ heterocycloalkyl, aryl, $C_1$-$C_{50}$ polyether, $C_1$-$C_{50}$ substituted alkyl, $C_3$-$C_8$ substituted cycloalkyl, $C_2$-$C_{50}$ substituted alkenyl, $C_2$-$C_{50}$ substituted alkynyl, $C_2$-$C_7$ substituted heterocycloalkyl, substituted aryl, heteroaryl, substituted heteroaryl, and a structure of formula (II):

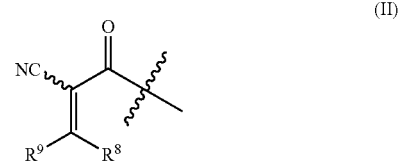

$R^9$ is (a) phenyl substituted with 0, 1, 2, 3, or 4 $R^{10}$ substituents or (b) 1-naphthyl or 2-naphthyl substituted with 0, 1, 2, 3, or 4 $R^{10}$ substituents; $R^6$ and $R^{10}$ are the same or different and are selected from the group consisting of hydrogen, hydroxyl, alkyl, alkenyl, alkynyl, alkoxy, halo, ester, nitro, nitroso, alkylcarbonyl, alkoxycarbonyl, aryl, amino, substituted amino, amido, substituted amido, sulfate, carboxylate, oxycarbonyl, cycloalkyl, haloalkyl, cyano, and thioether; $R^8$ is selected from the group consisting of hydrogen, $C_2$-$C_{50}$ alkyl, $C_2$-$C_{50}$ alkenyl, $C_2$-$C_{50}$ alkynyl, $C_3$-$C_8$ cycloalkyl, $C_2$-$C_7$ heterocycloalkyl, aryl, $C_1$-$C_{50}$ polyether, $C_1$-$C_{50}$ substituted alkyl, $C_3$-$C_8$ substituted cycloalkyl, $C_2$-$C_{50}$ substituted alkenyl, $C_2$-$C_{50}$ substituted alkynyl, $C_2$-$C_7$ substituted heterocycloalkyl, substituted aryl, heteroaryl, and substituted heteroaryl; and n is an integer from 1 to 500. Preferably, 4% by weight of a polymer terminated with an α-cyano β-p-methoxyphenyl β-napthyl acrylate is added to a sunscreen formulation containing 3% by weight of Avobenzone (i.e., a UV-A filter) and a plurality of UV-B filters. Preferably, the sunscreen compositions disclosed herein have a UV-A PFA value of at least about 8.0 as measured by the JCIA "Persistent Pigment Darkening" protocol, preferably in the range of about 10 to about 15.

Compounds of formula (I) (alternatively referred to as polyesters of formula (I)) can be prepared by the transesterification of a diester with a diol or by the esterification of a diacid with a diol, for example as shown below for one exemplary compound of formula (I):

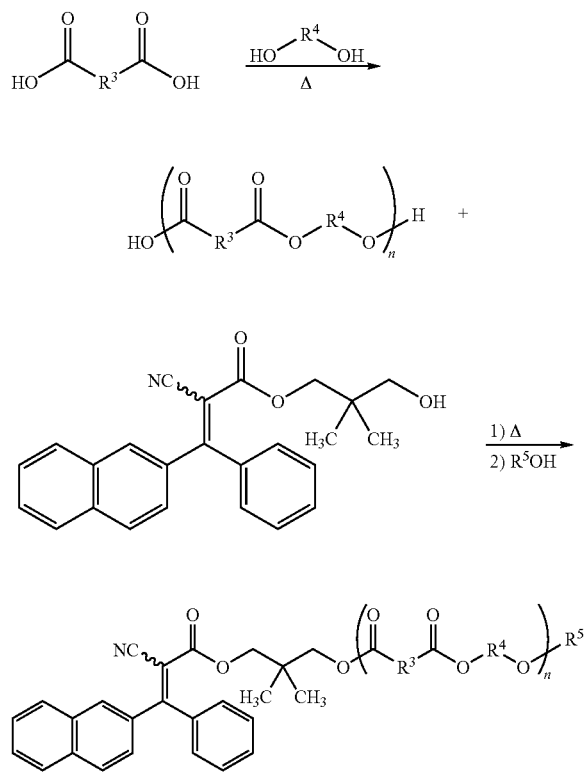

Transesterification or esterification can proceed to form a polymer under acidic, basic, or neutral conditions. When a polymer of formula (I) is prepared as shown above, the polymerization can be terminated with the addition of a compound, such as a alcohol, that cannot react any further to elongate the polymer chain. The alcohol $R^5OH$ can be either a cyanoacrylate or an aliphatic alcohol, or any other alcohol suitable for reaction under the conditions necessary to form the polyester polymer of compound (I).

EXAMPLES

The following examples are provided to illustrate the invention but are not intended to limit the scope of the invention.

Example 1

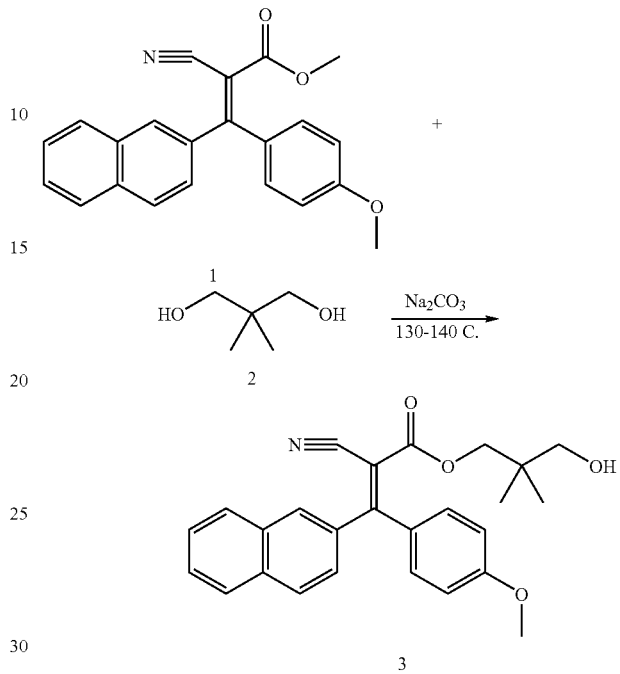

Procedure for the synthesis of alcohol 3: Methyl 2-cyano-3-(4'-methoxyphenyl)-3-(2"-naphthyl)propenoate (1 mole equivalent) is dissolved in excess of neopentyl glycol (NPG) (from 6 to 8 mole equivalent) placed in 3-neck round bottom flask, and sodium carbonate (0.03 mole equivalent) is added. Next, the reaction mixture is continuously stirred and heated at 135° C. to 150° C.; throughout reaction time, methanol is removed from the reaction mixture by continuous distillation applying continuous flow of nitrogen. When reaction is completed, typically within two hours, as monitored by gas chromatography (GC), xylenes are added to prevent solidification of the crude product mixture, and then sodium carbonate is filtered off while the solution is still hot. The xylenes solution is washed several times with water to remove completely the excess of glycol. Xylenes are then removed by distillation and the product is dried under vacuum. The crude product is purified by crystallization from toluene or ethyl acetate.

Synthesis of Polymer Derivative 1: Polymer Derivative 1, shown below, is prepared by combining the alcohol prepared in Example 1 with a polyester prepared from adipic acid and neopentyl glycol.

Polymer Derivative 1:

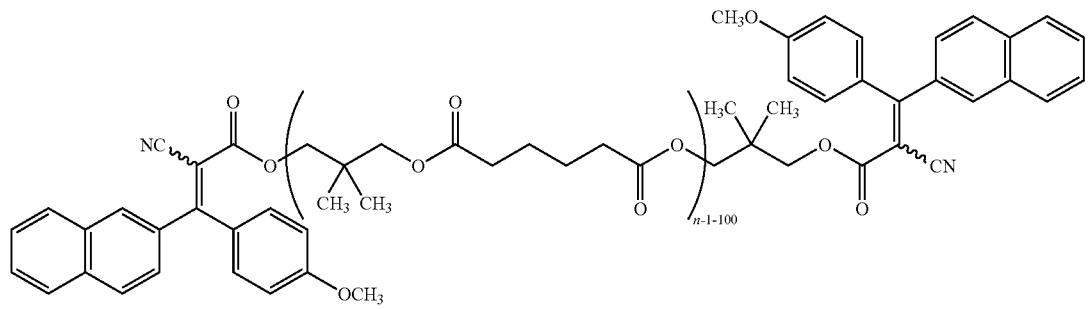

The following procedure was used to prepare Polymer Derivative 1: Adipic acid (3 moles equivalence) and NPG glycol were placed in 3-neck round-bottom flask, assembled with column and condenser for simple distillation to remove reaction water. The reaction mixture was then heated at 180-200° C. until the desired acid value was achieved (around AV=130).

Polymer Derivative 1, a polymer of the general formula $A(NA)_nA$, (1 mole equivalence; A=adipic acid and N=NPG (as shown above), NPG (2-cyano-3-(4'-methoxyphenyl)-3-(2"-naphthyl)propenoate) (1.5 mole equivalence), dibutyl ether, methane sulfonic acid catalyst (0.3% of the total batch weight), and an antioxidant (sodium hypophosphite; 0.03% of total batch weight) were placed in 3-neck round bottom flask. The reaction flask was assembled with mechanical stirrer, thermometer and nitrogen inlet, Dean-Stark adapter, and condenser. The reaction mixture was heated to temperature at which solvent refluxes, and the reflux was maintained for two hours. After two hours, 2-octyl-1-dodecanol (Isofol 20) (0.3 mole equivalence) was added and the reaction was refluxed for additional 2-4 hours. When the acid value of the reaction was less than 10, the solvent was removed by distillation. Next, sodium bicarbonate (0.5% of the total batch weight) was added to the reaction vessel, and the product was stirred for 30 minutes before filtration. The product was filtered through filtrating aid such as Celite at higher temperature. The UV absorbance spectrum of Polymer Derivative 1 was measured and is shown in FIG. 1.

Example 2

Two sunscreen compositions were prepared with the ingredients and in the amounts as indicated in Table II, and each was tested for UV absorbance and stability:

TABLE II

| | Ingredient | Polycrylene ® Composition (% by weight) | Polymer Derivative 1 Composition I (% by weight) |
|---|---|---|---|
| Oil Phase/UV Filters | | | |
| 1 | Polycrylene ® or Polymer Derivative 1 | 3.00 | 3.00 |
| 2 | Octisalate | 5.00 | 5.00 |
| 3 | Benzophenone-3 | 4.50 | 4.50 |
| 4 | Octocrylene | 2.50 | 2.50 |
| 5 | Diethylhexyl 2,6-naphthalate | 2.50 | 2.50 |
| 6 | Avobenzone | 3.00 | 3.00 |
| 7 | Steareth-21 | 0.60 | 0.60 |
| 8 | Steareth-2 | 0.50 | 0.50 |
| 9 | Cetearyl alcohol | 0.35 | 0.35 |
| 9a | Glyceryl stearate & PEG-100 stearate | 0.00 | 0.00 |
| 10 | $C_{30}$-$C_{38}$ olefin/isopropyl maleate/methacrylate copolymer | 0.80 | 0.80 |
| 11 | Potassium cetyl phosphate/hydrogenated palm glycerides | 3.00 | 3.00 |
| Water Phase | | | |
| 12 | Disodium EDTA | 0.10 | 0.10 |
| 13 | Tromethamine | 0.04 | 0.04 |
| 14 | Butylene glycol | 3.50 | 3.50 |
| 15 | Phenoxyethanol, Methyl paraben, Ethyl paraben, Propyl paraben, and Isobutyl paraben | 0.60 | 0.60 |

TABLE II-continued

| | Ingredient | Polycrylene ® Composition (% by weight) | Polymer Derivative 1 Composition I (% by weight) |
|---|---|---|---|
| Other Ingredients | | | |
| 16 | Acrylamide/sodium acryloyldimethyltaurate copolymer/isohexadecane/Polysorbate 80 | 2.00 | 2.00 |
| 17 | Methyl trimethicone | 4.00 | 4.00 |
| 18 | Dimethicone/Polysilicone-11 | 2.00 | 2.00 |
| 19 | Aluminum starch octenylsuccinate | 2.50 | 2.50 |
| 20 | Water | q.s. | q.s. |

In a vessel, ingredients 1-5 were combined, followed by the addition of 6 and 7. This oil mixture was heated to about 95° C. Then, ingredients 8-11 were added. In a second vessel, water (about 52.01% by weight) was mixed with ingredient 12 until 12 dissolved. Then, 13 was added, and the mixture heated to about 90° C. In a third vessel, ingredients 14 and 15 were premixed and then added to the second vessel. The mixture of the first vessel and of the second vessel were mixed together when the first vessel was at about 90° C. and the second vessel was at about 93° C. The oil phase (first vessel) was added to the water phase (second vessel) with stirring and without aeration. After ten minutes, the resulting mixture was homogenized and cooled. When the mixture was at about 50° C., homogenization was stopped, and sweep mixing commenced. When the mixture was at about 45° C., 16 was added. In a fourth vessel, 18 was diluted in 17, and when uniform, added to the mixture. After incorporation of the 17 and 18 mixture, ingredient 19 was added, then water as needed to correct for evaporative losses. Stirring was continued until the mixture was smooth and homogeneous.

Figure 2:
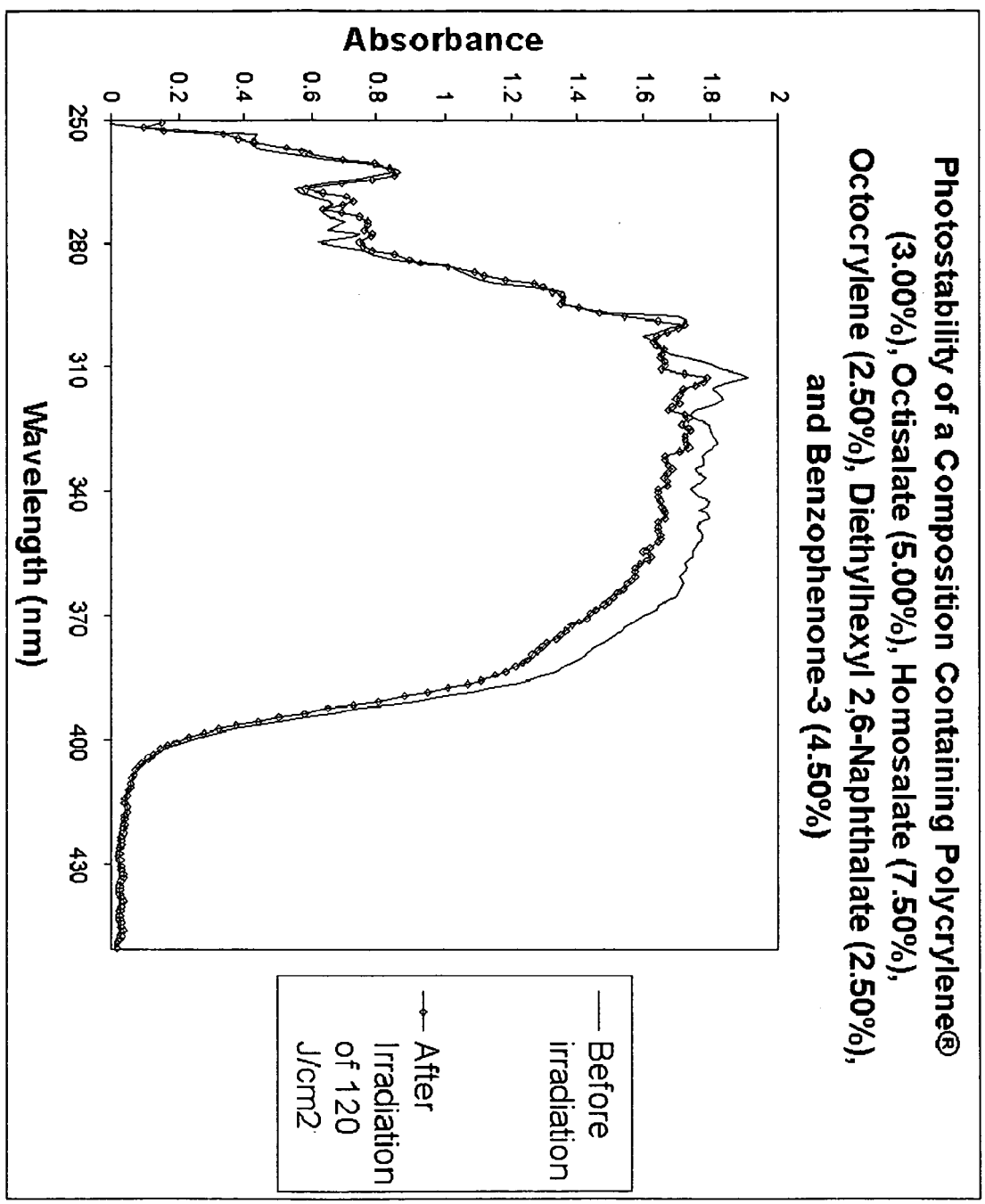
FIG. 2 is a graph of the absorbance of a sunscreen composition that includes 3% by weight of Polycrylene® and 3% by weight avobenzone before and after irradiation of 120 J/cm².
Figure 3:
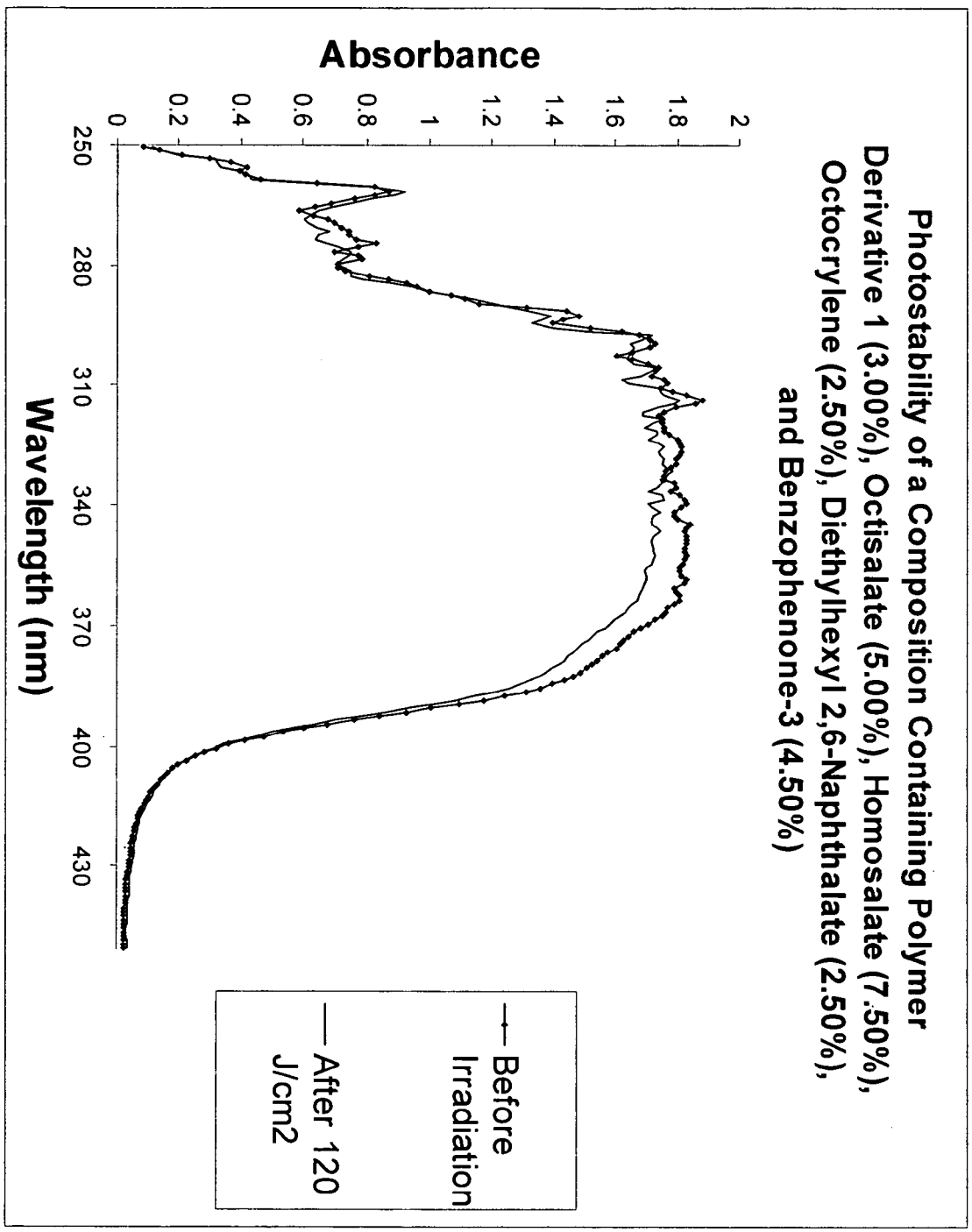
FIG. 3 is a graph of the absorbance of a sunscreen composition that includes 3% by weight of Polymer Derivative 1 (an α-cyano β-p-methoxyphenyl β-napthyl acrylate terminated polymer) and 3% by weight avobenzone before and after irradiation of 120 J/cm².

FIGS. 1 and 2 show the photostability of a sunscreen composition that includes Polycrylene® (FIG. 2) and Polymer Derivative 1 (FIG. 3). Photostability is assessed by measuring the absorbance on a Labsphere UV-1000S Ultraviolet Transmittance Analyzer (softer version 1.27) before and after irradiation with a Solar Light Company model 16S solar simulator (equipped with a WG 320 filter to transmit radiation greater than 290 nm). The radiation dose used was 35 MED. Output was monitored by a PMA 2105 UV-B DCS Detector (biologically weighted) and controlled by a PMA 2100 Automatic Dose Controller (Solar Light Co.).

To test stability, a slide is positioned on the UV transmittance analyzer using registration marks, and a scan of a 1 cm spot on the slide is performed. The slide is prepared with a synthetic skin substrate used for testing sunscreen compositions (VITRO-SKIN substrate by IMS, Inc. of Milford, Conn.). To prepare the substrate, a 300 g solution of 18 wt % glycerin and 82 wt % deionized water was added to a hydrating chamber (IMS), and a sheet of VITRO-SKIN was placed in the hydrating chamber and left overnight (approximately 16 hours). Several 6.5 cm squares were cut from the hydrated VITRO-SKIN and these squares were used for absorbance measurements.

To prepare the slide for testing, a minimum 100 μl of sunscreen composition is drawn or placed into a pipette tip (Justor 1100DG, set to dispense 100 μl). Using steady, even pressure on the pipette plunger, the test substance was applied to VITRO-SKIN square in a pattern of at least 50 small dots arranged to cover a 6 cm center of a square. The VITRO- SKIN square was then placed on a foam block, and the test material was spread by finger (covered with a latex glove or finger cot), first in a circular motion, then by a side-to-side motion during which the VITRO-SKIN is deformed by the pressure. The square was then mounted in a slide holder (60 mm×60 mm glassless slide mounts with metal masks by Gepe Management AG, Zug, Switzerland) and allowed to dry for 30-60 minutes.

To test stability of a slide in the UV-B range, the slide was positioned on the UV transmittance analyzer using registration marks, and a scan of a 1 cm spot on the slide was performed. The slide was then transferred to a holder placed adjacent to the solar simulator and, using a calipers, was positioned such that the beam of UV radiation exiting the solar simulator illuminated the same 1 cm spot on the slide. To test stability of a slide in the UV-A range, a WG335 filter was installed in the beam path. The following software settings were used: UV-B=290-320 nm; UV-A=320-400 nm. Following an exposure of 35 MED for the UV-B studies and 120 J/cm$^2$ for the UV-A studies, the slide was again placed in position on the UV transmittance analyzer, and a scan of the exposed spot was performed.

FIG. 2 is a graph of the absorbance of the first sunscreen composition listed in Table II, before and after exposure to 120 J/cm$^2$ irradiation. As seen in FIG. 2, the sunscreen composition containing 3% Polycrylene® and 3% avobenzone maintained its absorbance characteristics after 120 J/cm$^2$ irradiation.

FIG. 3 is a graph of the absorbance of the second sunscreen composition listed in Table II, before and after exposure to 120 J/cm$^2$ irradiation. As seen in FIG. 3, the sunscreen composition including 3% Polymer Derivative 1 and 3% avobenzone maintains its absorbance properties after irradiation of 120 J/cm$^2$.

A determination of the Sun Protection Factor (SPF) of the sunscreen compositions listed in Table II was performed. To test the SPF of the compositions, each slide is placed on the UV transmittance analyzer and scans are taken from five locations on the slide. An SPF report was generated for each slide using the Labsphere software UV1000S, Version 1.27. The first composition of Table II had an average SPF of 45.25, while the average SPF of the second composition of Table II (the Polymer Derivative 1 composition) was 47.94.

Example 3

Two sunscreen compositions were prepared in a similar fashion to the compositions listed in Table II. The first, composition A, contained 4% by weight of Polymer Derivative 1, 3% by weight of Avobenzone (a U-VA filter), and a plurality of UV-B filters. In addition, 2.5% by weight of Octocrylene and 2.5% by weight of Diethylhexyl 2,6-naphthalate were also added to composition A.

Composition B contained 3% by weight of Polycrylene®, 3% by weight of Avobenzone (a U-VA filter), and a plurality of UV-B filters. In addition, 2.5% by weight of Octocrylene and 2.5% by weight of Diethylhexyl 2,6-naphthalate were also added to composition B.

The UV-A Protection Value of the composition A was studied by the Persistent Pigment Darkening (PPD) method in accordance with the procedures set forth by the Japan Cosmetic Industry Association. The results of the PPD method for composition A are shown in Table III below, wherein composition A is designated "CAB5-233":

TABLE III

APPENDIX
Individual PFA Values

| Subject | | CPTC# | Skin Type | Age/Sex | |
|---|---|---|---|---|---|
| | | | | | Standard 180 Minutes |
| 1 | IM | 48458 | III | 35 M | 3.00 |
| 2 | DL | 28049 | III | 49 F | 3.75 |
| 3 | SC | 39559 | IV | 37 M | 4.68 |
| 4 | JC | 26996 | III | 34 M | 3.75 |
| 5 | MM | 48425 | III | 49 M | 3.00 |
| Average PFA (n = 5) | | | | | 3.64 |
| (95% Confidence Limits) | | | | | (2.78-4.50) |
| Standard Deviation | | | | | 0.69 |
| Standard Error | | | | | 0.31 |
| | | | | | CAB5-233 180 Minutes |
| 1 | IM | 48458 | III | 35 M | 12.51 |
| 2 | DL | 28049 | III | 49 F | 15.63 |
| 3 | SC | 39559 | IV | 37 M | 7.99 |
| 4 | JC | 26996 | III | 34 M | 15.63 |
| 5 | MM | 48425 | III | 49 M | 10.01 |
| Average PFA (n = 5) | | | | | 12.35 |
| (95% Confidence Limits) | | | | | (8.14-16.56) |
| Standard Deviation | | | | | 3.39 |
| Standard Error | | | | | 1.52 |

As shown in Table III, composition A was tested according to the PPD protocol on five subjects ranging in age from 35 to 49 years old. The standard formulation as set forth in the PPD protocol resulted in an average UV-Protection Value of 3.64. As determined by the PPD method, composition A had an average UV-Protection Value of 12.35, a value that is 3.4 times that of the average measured for the standard formulation on the same subjects.

The UV-A Protection Value of Composition B was also studied by the Persistent Pigment Darkening (PPD) method in accordance with the procedures set forth by the Japan Cosmetic Industry Association: The results of the PPD method for composition B are shown in Table IV below, wherein composition B is designated "CAB5-214":

TABLE IV

APPENDIX
Individual PFA Values

| Subject | | CPTC# | Skin Type | Age/Sex | |
|---|---|---|---|---|---|
| | | | | | Standard 180 Minutes |
| 1 | NJ | 49744 | IV | 19 F | 4.69 |
| 2 | PK | 20627 | III | 45 F | 5.86 |
| 3 | KM | 12453 | III | 59 F | 3.76 |
| 4 | FL | 48147 | IV | 34 F | 3.75 |
| 5 | PM | 49821 | III | 45 M | 3.75 |
| Average PFA (N = 5) | | | | | 4.36 |
| (95% Confidence Limits) | | | | | (3.20-5.52) |
| Standard Deviation | | | | | 0.93 |
| Standard Error | | | | | 0.42 |
| | | | | | CAB5-214 180 Minutes |
| 1 | NJ | 49744 | IV | 19 F | 8.76 |
| 2 | PK | 20627 | III | 45 F | 10.94 |
| 3 | KM | 12453 | III | 59 F | 10.94 |
| 4 | FL | 48147 | IV | 34 F | 10.94 |

TABLE IV-continued

APPENDIX
Individual PFA Values

| Subject | CPTC# | Skin Type | Age/Sex | |
|---|---|---|---|---|
| 5 PM | 49821 | III | 45 M | 10.95 |
| Average PFA (N = 5) | | | | 10.51 |
| (95% Confidence Limits) | | | | (9.30-11.72) |
| Standard Deviation | | | | 0.98 |
| Standard Error | | | | 0.44 |

As shown in Table IV, composition B was tested according to the PPD protocol on five subjects ranging in age from 19 to 59 years old. The standard formulation as set forth in the PPD protocol resulted in an average UV-Protection Value of 4.36. As determined by the PPD method, composition B had an average UV-Protection Value of 10.51, a value that is 2.4 times that of the average measured for the standard formulation on the same subjects.

These results show that the addition of a polymer terminated with a α-cyano acrylates, acrylamides, and/or thioacrylates, such as a compound of formula (I), can substantially improve the UV-A Protection Value of a sunscreen.

Example 4

A sunscreen composition was prepared with the ingredients and in the amounts indicated in Table V, and was tested for UV absorbance and stability:

TABLE V

| | Ingredient | Polymer Derivative 1 Composition II (% by weight) |
|---|---|---|
| | Oil Phase/UV Filters | |
| 1 | Avobenzone | 3.00% |
| 2 | Oxybenzone | 4.00% |
| 3 | Bemotrizinol (Tinosorb S) | 0.75% |
| 4 | Octisalate | 5.00% |
| 5 | Homosalate | 6.50% |
| 6 | Octocrylene | 2.50% |
| 7 | Diethylhexyl 2,6-naphthalate | 2.50% |
| 8 | Dimethyl capramide | 1.00% |
| 9 | Polymer Derivative 1 | 3.25% |
| 10 | Benzyl alcohol | 0.60% |
| 11 | $C_{30-38}$ Olefin/Isopropyl maleate/MA copolymer | 0.80% |
| 12 | Cetearyl alcohol | 0.35% |
| | Emulsifiers | |
| 13 | Glyceryl stearate & PEG-100 stearate | 2.50% |
| 14 | Potassium cetyl phosphate & Hydrogenated palm glycerides | 1.50% |
| | Water Phase (w/o emulsifiers) | |
| 15 | Butylene glycol | 4.00% |
| | Phenoxyethanol & Methyl paraben & Ethyl paraben & Propyl paraben & Isobutyl | |
| 16 | paraben | 0.60% |
| 17 | Triethanolamine | 0.60% |
| 18 | Ensulizole (pre-neutralized with NaOH) (15% solution) | 5.00% |
| 19 | Disodium EDTA | 0.10% |

TABLE V-continued

| | Ingredient | Polymer Derivative 1 Composition II (% by weight) |
|---|---|---|
| | Other Ingredients | |
| 20 | Carbomer (Ultrez ® 10) | 0.20% |
| 21 | Acrylamide/Sodium acryloyldimethyl taurate copolymer & Isohexadecane & Polysorbate 80 | 1.75% |
| 22 | Aluminum starch octenyl succinate | 2.50% |
| | Water | 51.00% |

A 500 gram batch of the formulation was made as follows: 100 grams of a stock 15% solution of Ensulizole (ingredient 18) was prepared in a vessel by dissolving 1.5 grams of NaOH (99%) in 82.8 grams of deionized water. Phenylbenzimidazole sulfonic acid (15 grams) was added to the vessel and the mixture was allowed to stir until the solution was clear.

The carbomer (ingredient 20) was pre-wetted in a second vessel by adding it to 20 grams of water and allowing it to stand for 15 minutes. Ingredients 15-17 were added to a third vessel and stirred until clear and homogeneous. In a fourth vessel, the oil phase was prepared by combining ingredients 1-9 with stirring and heating to about 95° C. Ingredient 11-14 were added and stirred until homogeneous.

In the primary vessel, the water phase was prepared by dissolving ingredient 19 in about 250 grams of deionized water and heating the solution to about 90° C.

Immediately before combining the oil and water phases, ingredient 10 was added to the oil phase with string. The emulsion was made by adding the oil phase to the water phase, removing it from heat, and stirring for 10 minutes. The emulsion was then homogenized for 10 minutes, during which the pre-wetted carbomer (ingredient 20) was added. After 10 minutes of homogenization, sweep stirring commenced, and when the temperature of the batch was about 45° C., (pre-mixed) ingredients 15-17 were added, followed by ingredients 18, 21, and 22. When the temperature of the batch was about 35° C., water was added to correct for evaporative losses. Stirring continued until the mixture was smooth and homogeneous.

Figure 4:
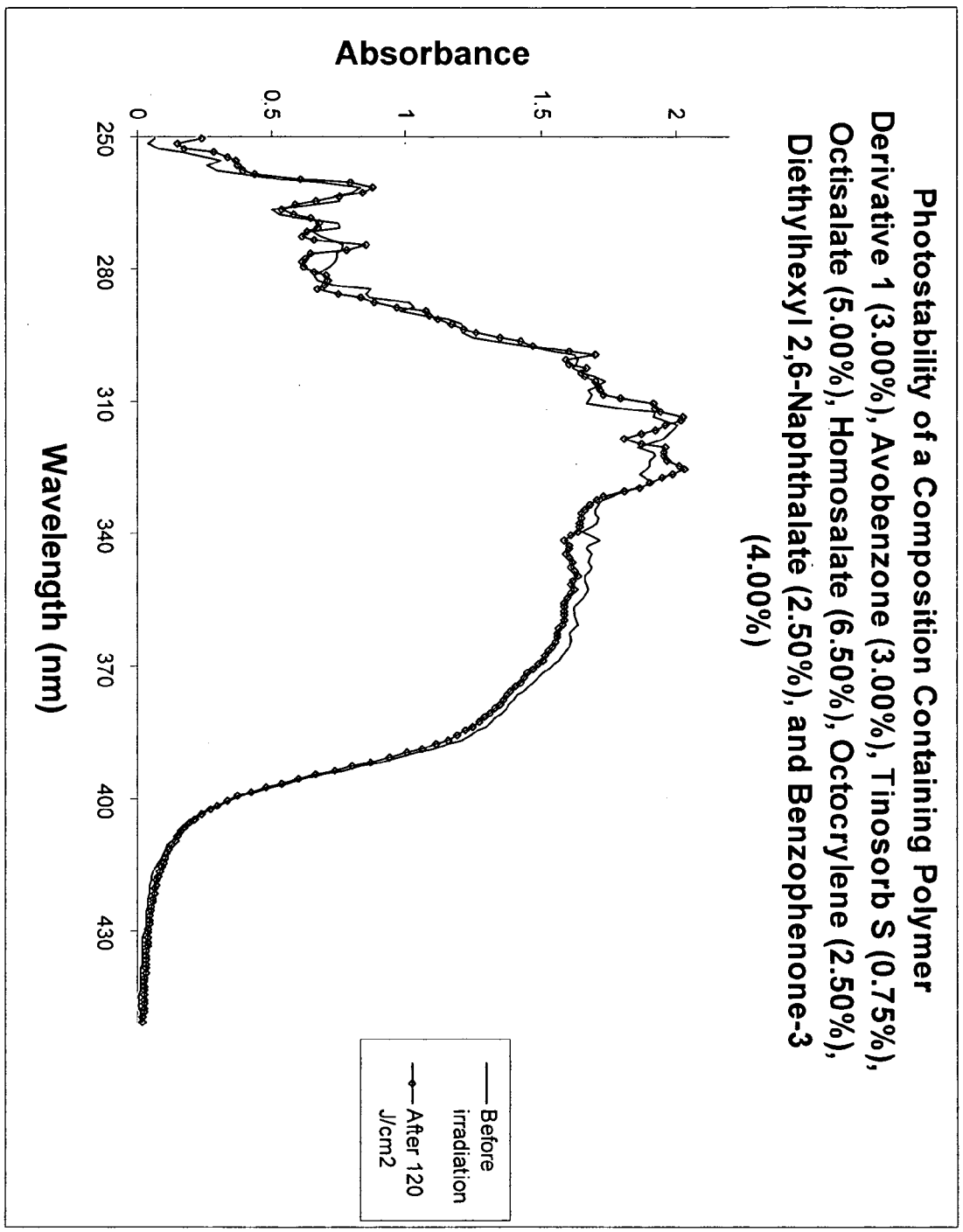
FIG. 4 is a graph of the absorbance of a sunscreen composition that includes 3% by weight of Polymer Derivative 1, 0.75% by weight Tinosorb S, and 3% by weight avobenzone before and after irradiation of 120 J/cm².

FIG. 4 show the photostability of the sunscreen composition that includes Polymer Derivative 1 and other UV absorbing agents as listed in Table V. Photostability was assessed by measuring the absorbance on a Labsphere UV-1000S Ultraviolet Transmittance Analyzer (softer version 1.27) before and after irradiation with a Solar Light Company model 16S solar simulator (equipped with a WG 3335 filter to transmit radiation greater than 320 nm). The radiation dose used was 120 J/cm$^2$. Output was monitored by a PMA 2114 UV-A DCS Detector and controlled by a PMA 2100 Automatic Dose Controller (Solar Light Co.).

To test stability, a slide is positioned on the UV transmittance analyzer using registration marks, and a scan of a 1 cm spot on the slide is performed. The slide is prepared with a synthetic skin substrate used for testing sunscreen compositions (VITRO-SKIN substrate by IMS, Inc. of Milford, Conn.). To prepare the substrate, a 300 g solution of 18 wt % glycerin and 82 wt % deionized water was added to a hydrating chamber (IMS), and a sheet of VITRO-SKIN was placed in the hydrating chamber and left overnight (approximately 16 hours). Several 6.5 cm squares were cut from the hydrated VITRO-SKIN and these squares were used for absorbance measurements.

To prepare the slide for testing, a minimum 100 µl of sunscreen composition is drawn or placed into a pipette tip (Justor 1100DG, set to dispense 100 µl). Using steady, even pressure on the pipette plunger, the test substance was applied to VITRO-SKIN square in a pattern of at least 50 small dots arranged to cover a 6 cm center of a square. The VITRO-SKIN square was then placed on a foam block, and the test material was spread by finger (covered with a latex glove or finger cot), first in a circular motion, then by a side-to-side motion during which the VITRO-SKIN is deformed by the pressure. The square was then mounted in a slide holder (60 mm×60 mm glassless slide mounts with metal masks by Gepe Management AG, Zug, Switzerland) and allowed to dry for 30-60 minutes.

To test stability of a slide in the UV-A range, a WG335 filter was installed in the beam path. The following software settings were used: UV-B=290-320 nm; UV-A=320-400 nm. Following an exposure 120 J/cm² for the UV-A studies, the slide was again placed in position on the UV transmittance analyzer, and a scan of the exposed spot was performed.

FIG. 4 is a graph of the absorbance of the first sunscreen composition listed in Table V, before and after exposure to 120 J/cm² of UV radiation, 320-400 nm. As seen in FIG. 4, the sunscreen composition containing 3.25% Polymer Derivative 1 maintained its absorbance characteristics after 120 J/cm² irradiation. This represents an improvement in photostability over the example shown in FIG. 3, which may be attributable to the presence of Bemotrizinol (Tinosorb S) and, perhaps, Ensulizole, in the formulation. Bemotrizinol is well-known for its photostabilizing properties.

A determination of the Sun Protection Factor (SPF) of the sunscreen composition listed in Table V was performed. To test the SPF of the compositions, each slide is placed on the UV transmittance analyzer and scans are taken from five locations on the slide. An SPF report was generated for each slide using the Labsphere software UV1000S, Version 1.27. The composition of Table V had an average SPF of 48.26.

The foregoing description is given for clearness of understanding only, and no unnecessary limitations should be understood therefrom, as modifications within the scope of the compounds, compositions, and methods described herein may be apparent to those having ordinary skill in the art.

What is claimed is:
1. A compound of formula (I):

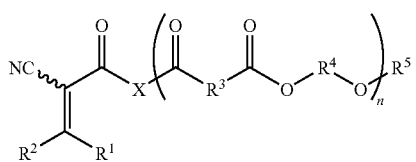

(I)

wherein $R^2$ is (a) phenyl substituted with 0, 1, 2, 3, or 4 $R^6$ substituents or (b) 1-naphthyl or 2-naphthyl substituted with 0, 1, 2, 3, or 4 $R^6$ substituents; $R^1$ is selected from the group consisting of aryl and substituted aryl; $R^3$ and $R^4$ are the same or different and are selected from the group consisting of $C_1$-$C_{30}$ alkyl, $C_3$-$C_8$ cycloalkyl, substituted alkyl, substituted cycloalkyl, aryl, heteroaryl, heterocycloalkyl, substituted aryl, substituted heteroaryl, and substituted heterocycloalkyl;

X is selected from the group consisting of O—$C_1$-$C_{20}$ alkyl-O—, N($R^7$)-$C_1$-$C_{20}$ alkyl-N($R^7$)—, and S—$C_1$-$C_{20}$ alkyl-S—; $R^7$ is selected from the group consisting of hydrogen and $C_1$-$C_{20}$ alkyl; $R^5$ is a structure of formula (II):

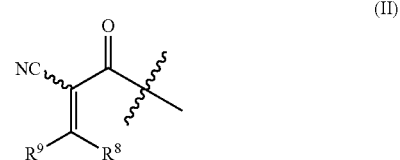

(II)

$R^9$ is (a) phenyl substituted with 0, 1, 2, 3, or 4 $R^{10}$ substituents or (b) 1-naphthyl or 2-naphthyl substituted with 0, 1, 2, 3, or 4 $R^{10}$ substituents; $R^6$ and $R^{10}$ are the same or different and are selected from the group consisting of hydrogen, hydroxyl, alkyl, alkenyl, alkynyl, alkoxy, halo, ester, nitro, nitroso, alkylcarbonyl, alkoxycarbonyl, aryl, amino, substituted amino, amido, substituted amido, sulfate, carboxylate, oxycarbonyl, cycloalkyl, haloalkyl, cyano, and thioether; $R^8$ is selected from the group consisting of aryl, and substituted aryl;

and n is an integer from 1 to 500.

2. The compound of claim 1, wherein $R^1$ is selected from the group consisting of aryl and substituted aryl.

3. The compound of claim 1, wherein $R^1$ is selected from the group consisting of naphthyl, phenyl, substituted naphthyl, and substituted phenyl.

4. The compound of claim 3, wherein said substituted aryl and said substituted napthyl are substituted with an electron donating substituent selected from the group consisting of alkyl, alkenyl, aryl, alkoxy, amino, alkylamino, thioether, hydroxyl, oxycarbonyl, and amido.

5. The compound of claim 1, wherein $R^2$ is 1-naphthyl or 2-naphthyl substituted with 0, 1, 2, 3, or 4 $R^6$ substituents.

6. The compound of claim 1, wherein $R^2$ is phenyl substituted with 0, 1, 2, 3, or 4 $R^6$ substituents.

7. The compound of claim 1, wherein $R^6$ and $R^{10}$ are each electron donating substituents selected from the group consisting of alkyl, alkenyl, aryl, alkoxy, amino, thioether, hydroxyl, oxycarbonyl, and amido.

8. The compound of claim 1, wherein X is O—$C_1$-$C_{20}$ alkyl-O—.

9. The compound of claim 8, wherein X is selected from the group consisting of

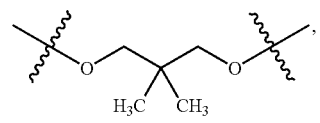

,

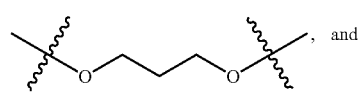

, and

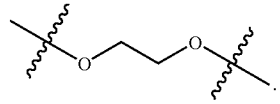

.

10. The compound of claim 1, wherein said compound of formula (I) is:

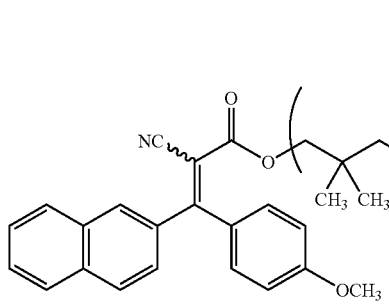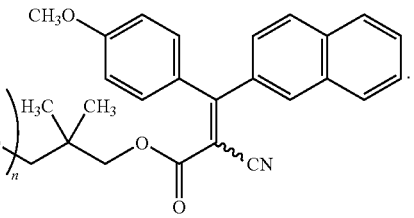

11. A method of protecting human skin from ultra-violet radiation comprising applying a compound of claim 1 in a cosmetically acceptable carrier to said human skin.

12. A method of photostabilizing a dibenzoylmethane derivative in a composition, said method comprising the step of adding to said dibenzoylmethane derivative a photostabilizing amount of a compound of claim 1.

13. The method of claim 12, wherein said composition further comprises a photoactive compound selected from the group consisting of bis-ethylethoxyphenol-methoxyphenol triazine, methylene bis-benzotriazolyl tetramethylbutyl phenol, diethylamino-hydroxybenzoyl-hexyl benzoate, disodium phenyldibenzimidazoletetrasulfonate, octocrylene, di-octyl-naphthalate, and combinations thereof.

14. A method of quenching triplet excited state energy from a triplet-excited photoactive compound in a sunscreen composition comprising adding to said composition a compound of claim 1.

15. A sunscreen composition, comprising a mixture of a photoactive compound and a compound of claim 1.

16. The composition of claim 15, wherein said photoactive compound is selected from the group consisting of bis-ethylethoxyphenol-methoxyphenol triazine, methylene bis-benzotriazolyl tetramethylbutyl phenol, diethylamino-hydroxybenzoyl-hexyl benzoate, disodium phenyldibenzimidazoletetrasulfonate, octocrylene, di-octyl-naphthalate, and combinations thereof.

17. The composition of claim 15, wherein $R^1$ is selected from the group consisting of aryl and substituted aryl.

18. The composition of claim 15, wherein $R^1$ is selected from the group consisting of naphthyl, phenyl, substituted naphthyl, and substituted phenyl.

19. The composition of claim 15, wherein $R^2$ is 1-naphthyl or 2-naphthyl substituted with 0, 1, 2, 3, or 4 $R^6$ substituents.

20. The composition of claim 15, wherein $R^2$ is phenyl substituted with 0, 1, 2, 3, or 4 $R^6$ substituents.

21. The composition of claim 16, wherein $R^6$ and $R^{10}$ are each electron donating substituents selected from the group consisting of alkyl, alkenyl, aryl, alkoxy, amino, alkylamino, thioether, hydroxyl, oxycarbonyl and amido.

22. The composition of claim 15, wherein X is O—$C_1$-$C_{20}$ alkyl-O—.

23. The composition of claim 22, wherein X is selected from the group consisting of

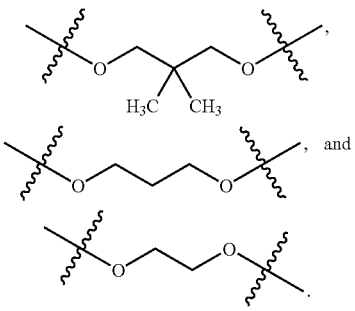

24. The composition of claim 15, wherein the photoactive compound is selected from the group consisting of p-aminobenzoic acid and salts and derivatives thereof; anthranilate and derivatives thereof; dibenzoylmethane and derivatives thereof; salicylate and derivatives thereof; cinnamic acid and derivatives thereof; dihydroxycinnamic acid and derivatives thereof; camphor and salts and derivatives thereof; trihydroxycinnamic acid and derivatives thereof; dibenzalacetone naphtholsulfonate and salts and derivatives thereof; benzalacetophenone naphtholsulfonate and salts and derivatives thereof; dihydroxy-naphthoic acid and salts thereof; o-hydroxydiphenyldisulfonate and salts and derivatives thereof; p-hydroxydiphenyldisulfonate and salts and derivatives thereof; coumarin and derivatives thereof; diazole derivatives; quinine derivatives and salts thereof; quinoline derivatives; hydroxy-substituted benzophenone derivatives; methoxy-substituted benzophenone derivatives; uric acid derivatives; vilouric acid derivatives; tannic acid and derivatives thereof; hydroquinone; benzophenone derivatives; 1,3,5-triazine derivatives; phenyldibenzimidazole tetrasulfonate and salts and derivatives thereof; terephthalylidene dicamphor sulfonic acid and salts and derivatives thereof; methylene bis-benzotriazolyl tetramethylbutylphenol and salts and derivatives thereof; bis-ethylhexyloxyphenol methoxyphenyl triazine and salts and derivatives thereof; diethylamino hydroxybenzoyl hexyl benzoate and salts and derivatives thereof; and combinations of the foregoing.

25. The composition of claim 15, wherein the photoactive compound is a dibenzoylmethane derivative.

26. The composition of claim 25, wherein said dibenzoylmethane derivative is selected from the group consisting of 2-methyldibenzoylmethane; 4 methyldibenzoylmethane; 4-isopropyldibenzoylmethane; 4-tert-butyldibenzoylmethane; 2,4-dimethyldibenzoylmethane; 2,5-dimethyldibenzoylmethane; 4,4'-diisopropyldibenzoylmethane; 4,4'-dimethoxydibenzoylmethane; 4-tert-butyl-4'-methoxydibenzoylmethane; 2-methyl-5-isopropyl-4'-methoxydibenzoylmethane; 2-methyl-5-tert-butyl-4'-methoxydibenzoylmethane; 2,4-dimethyl-4'-methoxydibenzoylmethane; 2,6-dimethyl-4-tert-butyl-4'-methoxydibenzoylmethane, and combinations thereof.

27. The composition of claim 15, wherein said photoactive compound is selected from the group consisting of bis-ethylethoxyphenol-methoxyphenol triazine, methylene bis-benzotriazolyl tetramethylbutyl phenol, diethylamino-hydroxybenzoyl-hexyl benzoate, disodium phenyldibenzimidazoletetrasulfonate, octocrylene, di-octyl-naphthalate, and combinations thereof.

28. The composition of claim 27, wherein said photoactive compound is bis-ethylethoxyphenol-methoxyphenol triazine.

29. The composition of claim 27, wherein said photoactive compound is methylene bis-benzotriazolyl tetramethylbutyl phenol.

30. The composition of claim 27, wherein said photoactive compound is diethylamino-hydroxybenzoyl-hexyl benzoate.

31. The composition of claim 27, wherein said photoactive compound is disodium phenyldibenzimidazoletetrasulfonate.

32. The composition of claim 27, wherein said photoactive compound is octocrylene.

33. The composition of claim 27, wherein said photoactive compound is di-octyl-naphthalate.

34. The composition of claim 15, wherein said composition has a UV-A Protection Value of at least about 8.0.

35. The composition of claim 34, wherein said composition has a UV-A Protection Value in the range of about 10.0 to about 15.0.

36. A compound of formula (III):

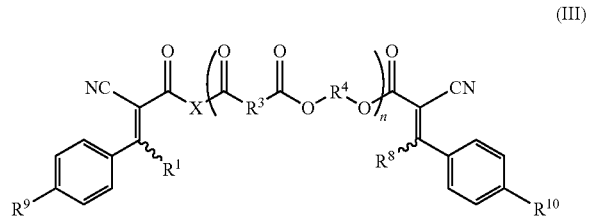

(III)

wherein $R^1$ and $R^8$ are the same or different and are selected from the group consisting of aryl and substituted aryl; $R^3$ and $R^4$ are the same or different and are selected from the group consisting of $C_1$-$C_{30}$ alkyl, $C_3$-$C_8$ cycloalkyl, substituted alkyl, substituted cycloalkyl, aryl, heteroaryl, heterocycloalkyl, substituted aryl, substituted heteroaryl, and substituted heterocycloalkyl; X is selected from the group consisting of O—$C_1$-$C_{20}$ alkyl-O—, N($R^7$)-$C_1$-$C_{20}$ alky-N($R^7$)—, and S—$C_1$-$C_{20}$ alkyl-S—; $R^7$ is selected from the group consisting of hydrogen and $C_1$-$C_{20}$ alkyl; $R^9$ and $R^{10}$ are the same or different and are each an electron donating group selected from the group consisting of alkyl, alkenyl, aryl, alkoxy, amino, alkylamino, thioether, hydroxyl, oxycarbonyl, and amido; and n is an integer from 1 to 500.

37. The compound of claim 36, wherein $R^1$ and $R^8$ are the same or different and are selected from the group consisting of phenyl, and substituted phenyl.

38. The compound of claim 36, wherein X is O—$C_1$-$C_{20}$ alkyl-O—.

39. The compound of claim 38, wherein X is selected from the group consisting of

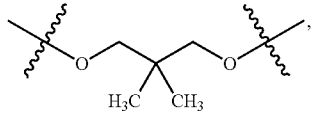,

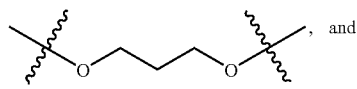, and

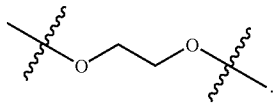.

40. The compound of claim 36, wherein said compound of formula (III) is:

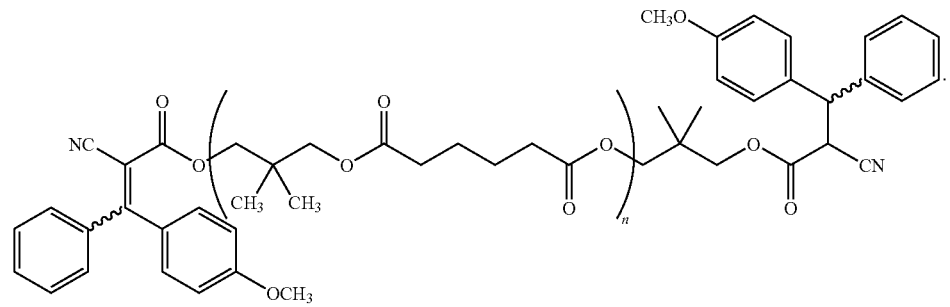

* * * * *